United States Patent
Inoue et al.

(10) Patent No.: US 10,758,134 B2
(45) Date of Patent: Sep. 1, 2020

(54) SENSOR, SENSOR APPARATUS, AND ELECTRONIC DEVICE

(71) Applicant: SHARP KABUSHIKI KAISHA, Sakai, Osaka (JP)

(72) Inventors: Takahiro Inoue, Sakai (JP); Nobuhiro Takahashi, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 360 days.

(21) Appl. No.: 15/321,045

(22) PCT Filed: May 27, 2015

(86) PCT No.: PCT/JP2015/065233
§ 371 (c)(1),
(2) Date: Dec. 21, 2016

(87) PCT Pub. No.: WO2016/017258
PCT Pub. Date: Feb. 4, 2016

(65) Prior Publication Data
US 2017/0196471 A1 Jul. 13, 2017

(30) Foreign Application Priority Data
Jul. 28, 2014 (JP) .................................. 2014-153062

(51) Int. Cl.
*A61B 5/024* (2006.01)
*A61B 5/00* (2006.01)
*H03M 1/52* (2006.01)

(52) U.S. Cl.
CPC ........ *A61B 5/02433* (2013.01); *A61B 5/6826* (2013.01); *A61B 5/725* (2013.01);
(Continued)

(58) Field of Classification Search
CPC .... G09G 3/36; G09G 5/10; G01J 1/44; A61B 5/02416; A61B 5/02438; A61B 5/1455;
(Continued)

(56) References Cited

U.S. PATENT DOCUMENTS 8,600,468 B2 * 12/2013 Yamamoto ......... A61B 5/02416
600/310
2005/0184895 A1 8/2005 Petersen et al.
(Continued)

FOREIGN PATENT DOCUMENTS

JP 7-294564 A 11/1995
JP 10-201743 A 8/1998
(Continued)

*Primary Examiner* — Jon Eric C Morales
(74) *Attorney, Agent, or Firm* — Birch, Stewart, Kolasch & Birch, LLP

(57) ABSTRACT

A sensor that is capable of detecting a pulse of a user by using a proximity illumination sensor or a proximity sensor is provided. A proximity sensor (14) that includes a pulse detection function includes a count adjustment circuit (5) that performs adjustment such that a digital output value (ADCOUT1) from an analog-digital conversion circuit (4) changes in accordance with each value of a distance at least in a prescribed range of the distance between a photodiode (2) and a detected object (a finger in the drawing) and a digital filter (6) for detecting a cycle of the digital output value (ADCOUT1) from the analog-digital conversion circuit (4).

11 Claims, 17 Drawing Sheets

(52) U.S. Cl.
 CPC ........ *A61B 5/7225* (2013.01); *A61B 5/02438* (2013.01); *H03M 1/52* (2013.01)

(58) Field of Classification Search
 CPC ..... A61B 5/4818; A61B 5/681; A61B 5/1112; A61B 5/02055; A61B 5/6823
 USPC .................. 600/310, 323, 324; 345/102, 207
 See application file for complete search history.

(56) References Cited

U.S. PATENT DOCUMENTS

| | | | |
|---|---|---|---|
| 2007/0114360 A1* | 5/2007 | Lim | G01J 1/32 250/205 |
| 2008/0023727 A1 | 1/2008 | Hoshi et al. | |
| 2012/0113074 A1* | 5/2012 | Inoue | G01J 1/1626 345/207 |
| 2015/0192664 A1* | 7/2015 | Sato | H03M 1/0607 250/206.1 |

FOREIGN PATENT DOCUMENTS

| | | | |
|---|---|---|---|
| JP | 2007-523727 A | 8/2007 |
| JP | 2008-34522 A | 2/2008 |
| JP | 2009-112625 A | 5/2009 |
| JP | 2012-104656 A | 5/2012 |

* cited by examiner

SENSOR, SENSOR APPARATUS, AND ELECTRONIC DEVICE

TECHNICAL FIELD

The present invention relates to a sensor that includes a proximity sensor, a proximity illumination sensor, and so forth, a sensor apparatus that includes the sensor and a light-emitting element which emits light including infrared light, and an electronic device that includes a proximity sensor, a proximity illumination sensor, and so forth.

BACKGROUND ART

It is desired that an illumination sensor is installed in a display unit that is included in a portable device such as a cellular phone, a smart phone, or a digital camera in order to adjust a light emission amount in accordance with the illumination of external light (ambient light).

It is also desired that a proximity sensor is installed in those portable devices in order to realize lower power consumption so that the display unit is turned off when a face of a user approaches.

In addition, a proximity and illumination sensor in which the illumination sensor and a proximity sensor are integrated has been suggested from a demand for size reduction of those portable devices.

It is strongly demanded that the sensors installed in those portable devices are used to perform detection of the pulse of the user as a new function (application) of those portable devices and a health condition may thereby be confirmed easily.

In related art, as disclosed in PTL 1, a method has been used in which light emitted by a light-emitting diode is received by a photodiode because reflected light that is reflected by a fingertip of a person changes in accordance with the blood flow, the change in the reflected light is detected, and the pulse is thereby detected. This pulse detection requests accurate detection of a signal cycle. Further, PTL 2 discloses pulse detection by using an analog-digital conversion circuit of an integrating type.

CITATION LIST

Patent Literature

PTL 1: Japanese Unexamined Patent Application Publication No. 7-294564 (laid open on Nov. 10, 1995)
PTL 2: Japanese Unexamined Patent Application Publication (Translation of PCT Application) No. 2007-523727 (laid open on Aug. 23, 2007)
PTL 3: Japanese Unexamined Patent Application Publication No. 2008-034522 (laid open on Feb. 14, 2008)
PTL 4: Japanese Unexamined Patent Application Publication No. 10-201743 (laid open on Aug. 4, 1998)

SUMMARY OF INVENTION

Technical Problem

FIG. 15 illustrates one example of a proximity illumination sensor in related art that is installed in a portable device such as a cellular phone or a smart phone.

As illustrated in the drawing, a proximity illumination sensor 101 includes an infrared light targeting photodiode 102 that has spectral characteristics for an infrared light region and a visible light to infrared light targeting photodiode 103 that has spectral characteristics for a region of visible light to infrared light, as light-receiving elements, and includes analog-digital conversion circuits 104 and 105 for converting input currents as analog values from the respective photodiodes 102 and 103 to digital values.

A function as a proximity sensor in the proximity illumination sensor 101 is the same as a proximity sensor 107, which will be described later. Thus, a description thereof will not be made, and only a function as an illumination sensor will be described here.

The current generated in accordance with a received light amount per unit time in the infrared light targeting photodiode 102 is set as an input current 1 (Iin1), and the current generated in accordance with the received light amount per unit time in the visible light to infrared light targeting photodiode 103 is set as an input current 2 (Iin2).

A digital value that is output from the analog-digital conversion circuit 104 as a result of analog-digital conversion of the input current 1 (Iin1) by the analog-digital conversion circuit 104 is ADCOUT1. A digital value that is output from the analog-digital conversion circuit 105 as a result of analog-digital conversion of the input current 2 (Iin2) by the analog-digital conversion circuit 105 is ADCOUT2.

Then, the computation of the subtraction of above ADCOUT1 that is multiplied by α from ADCOUT2 is performed, and the following illumination result may thereby be obtained as a digital value.

$$ADCOUT2-ADCOUT1\times\alpha=Iin2-Iin1\times\alpha$$

FIG. 16 illustrates one example of a proximity sensor in related art that is installed in a portable device such as a cellular phone or a smart phone.

An LED element 106 emits light that includes light at a prescribed wavelength to be received by the proximity sensor 107 in order to detect the degree of proximity of a detected object 110 and is also a backlight that irradiates a display panel 109 with light.

The proximity sensor 107 has a configuration that includes a photodiode (not illustrated) as a light-receiving element and an analog-digital conversion circuit (not illustrated).

Lenses 108 are provided on the photodiodes of the LED element 106 and the proximity sensor 107 and improve light-receiving efficiency and light-emitting efficiency.

FIG. 17 illustrates examples of control signals of the LED element and output values and determination values of the proximity sensor, which are illustrated in FIG. 16.

FIG. 17(a) is a case where the detected object 110 is in proximity of the proximity sensor 107. In a case where the LED element 106 is caused to emit light, because the detected object 110 is in proximity, reflected light from the detected object 110 is much, and the received light amount that is received by the photodiode of the proximity sensor 107 is high. Accordingly, an output value data of the proximity sensor 107 in a light-emitting period of the LED element 106 becomes Data1, and the output value data of the proximity sensor 107 in a non-light-emitting period of the LED element 106 becomes Data2. Further, the difference between those Data1 and Data2 is set as proximity data, and a determination is made that a state where the detected object 110 is in proximity to the proximity sensor 107 (proximity state) is present in a case where the proximity data is a threshold value or more.

On the other hand, FIG. 17(b) is a case where the detected object 110 is separated from the proximity sensor 107. Even if the LED element 106 is caused to emit light, because the detected object 110 is separated, the reflected light from the detected object 110 is low, and the received light amount that is received by the photodiode of the proximity sensor 107 is low. Accordingly, the output value data of the proximity sensor 107 in the light-emitting period of the LED element 106 becomes Data1, and the output value data of the proximity sensor 107 in the non-light-emitting period of the LED element 106 becomes Data2. Further, the difference between those Data1 and Data2 is set as the proximity data, and a determination is made that a state where the detected object 110 is separated from the proximity sensor 107 (non-proximity state) is present because the proximity data are less than the threshold value.

Because the above proximity illumination sensor 101 and proximity sensor 107 make a determination whether or not the detected object is present close to the proximity illumination sensor 101 or the proximity sensor 107, in a case where the detected object is present close to the proximity illumination sensor 101 or the proximity sensor 107 and even where the output value of the analog-digital conversion circuit is saturated, a proximity determination about the detected object is not largely influenced.

However, in a case where the pulse of a user is measured by using the proximity illumination sensor or the proximity sensor, because the measurement is performed by causing a finger of the user to approach the proximity illumination sensor or the proximity sensor, the output value of the analog-digital conversion circuit is saturated. In order to detect the pulse of the user, it is requested that cycle of the output value of the analog-digital conversion circuit is detected. In a case where the output value of the analog-digital conversion circuit is saturated, the cycle of the output value of the analog-digital conversion circuit may not be detected. This results in difficulty in detection of the pulse of the user.

As described above, the detection of the pulse of the user is different from the proximity determination about the detected object by using the proximity illumination sensor or the proximity sensor. It is thus difficult to detect the pulse of the user by using the proximity illumination sensor or the proximity sensor. Thus, the portable device or the like that includes a function of detecting the pulse of the user usually has to be provided with a separate pulse sensor for detecting the pulse of the user. This has been one of the causes that hinders size reduction and price reduction of the portable device.

An object of the present invention is to provide a sensor, a sensor apparatus, and an electronic device that are capable of detecting a pulse of a user by using a proximity illumination sensor or a proximity sensor.

Solution to Problem

To solve the above problems, a sensor of the present invention is a sensor that includes a first light-receiving element which receives infrared light and an analog-digital conversion circuit which converts an analog output value of the first light-receiving element to a digital output value, the sensor including an adjustment circuit that performs adjustment such that the digital output value changes in accordance with each value of a distance at least in a prescribed range of the distance between the first light-receiving element and a detected object, and a digital filter that detects a cycle of the digital output value.

The above configuration may realize a sensor that is capable of detecting a pulse of a user by using a proximity illumination sensor or a proximity sensor.

To solve the above problems, a sensor apparatus of the present invention includes the sensor and a light-emitting element that emits light which includes infrared light.

The above configuration may realize a sensor apparatus that is capable of detecting the pulse of the user by using the proximity illumination sensor or the proximity sensor.

To solve the above problems, an electronic device of the present invention is an electronic device including a sensor that includes a first light-receiving element which receives infrared light and an analog-digital conversion circuit which converts an analog output value of the first light-receiving element to a digital output value, in which the sensor includes an adjustment circuit that performs adjustment such that the digital output value changes in accordance with each value of a distance at least in a prescribed range of the distance between the first light-receiving element and a detected object, and a digital filter process is performed for the digital output value and a cycle thereof is detected.

The above configuration may realize an electronic device that is capable of detecting the pulse of the user by using the proximity illumination sensor or the proximity sensor.

Advantageous Effects of Invention

One aspect of the present invention may realize a sensor, a sensor apparatus, and an electronic device that are capable of detecting a pulse of a user by using a proximity illumination sensor or a proximity sensor.

DESCRIPTION OF EMBODIMENTS

Embodiments of the present invention will hereinafter be described in detail with reference to drawings. However, dimensions, materials, shapes, relative arrangement thereof, and so forth of configuration components described in the embodiments are only some embodiments. It should be noted that the scope of the present invention is not limitedly construed therefrom.

The embodiments of the present invention will be described below based on FIG. 1 to FIG. 14.

First Embodiment

One embodiment of the present invention will be described below based on FIG. 1 to FIG. 8.

Figure 1:
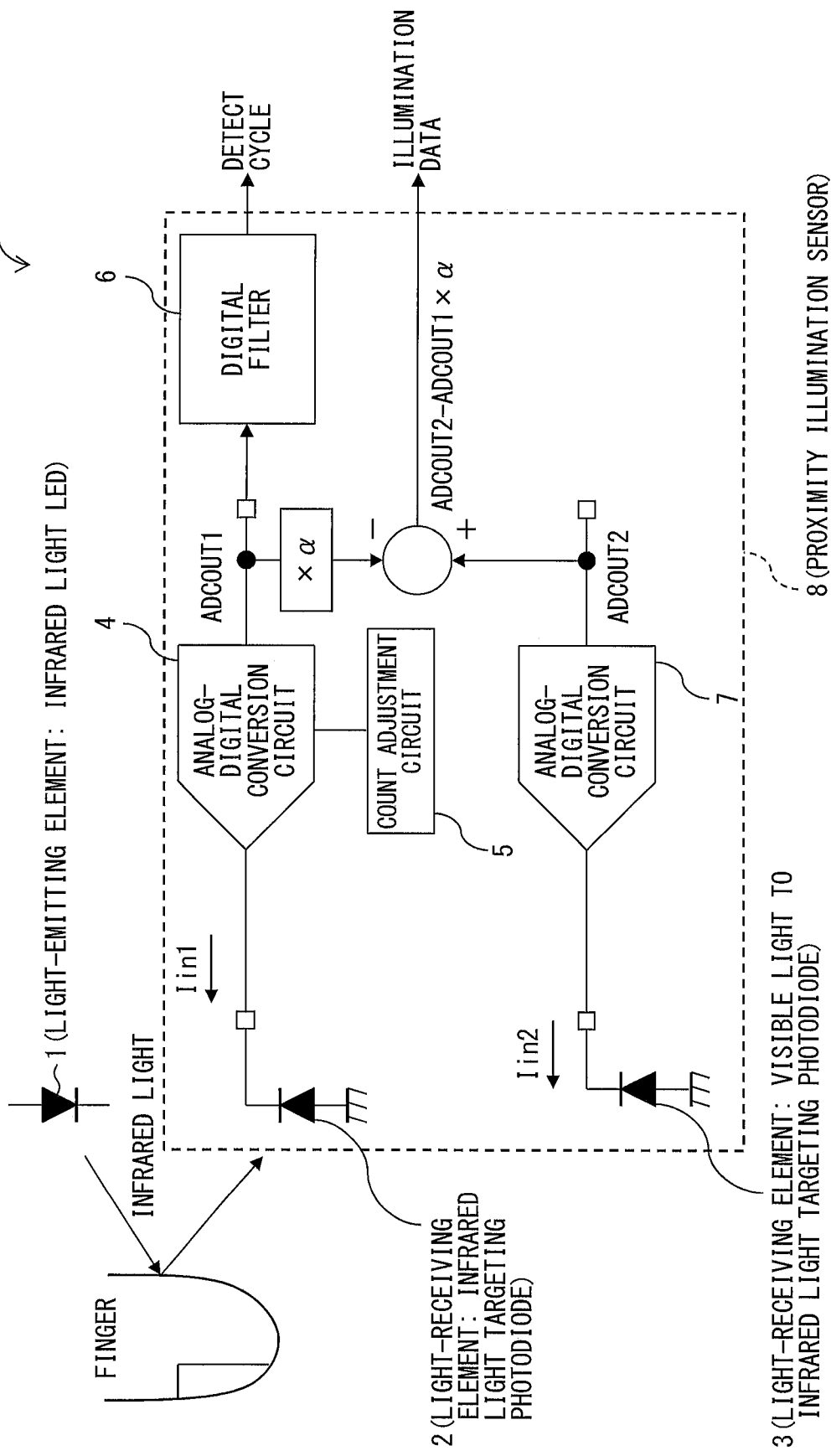
FIG. 1 is a diagram that illustrates a schematic configuration of a sensor apparatus that includes an infrared light LED as a light-emitting element and a proximity illumination sensor which includes a pulse detection function.

FIG. 1 is a diagram that illustrates a schematic configuration of a sensor apparatus 9 that includes an infrared light LED 1 as a light-emitting element and a proximity illumination sensor 8 which includes a pulse detection function.
(Light-Emitting Element)

In this embodiment, the infrared light LED 1 is used as the light-emitting element in consideration of a received light wavelength region of the proximity illumination sensor 8 that includes the pulse detection function. Hemoglobin in blood in a finger of a user has properties of properly absorbing near infrared light, and a light-emitting element that emits light including an infrared light region is preferably used.
(Proximity Illumination Sensor Including Pulse Detection Function)

As illustrated in FIG. 1, the proximity illumination sensor 8 that includes the pulse detection function includes an infrared light targeting photodiode 2 that has spectral characteristics for the infrared light region and a visible light to infrared light targeting photodiode 3 that has spectral characteristics for a region of visible light to infrared light, as light-receiving elements.

In addition, the proximity illumination sensor 8 that includes the pulse detection function includes an analog-digital conversion circuit 4 for converting an input current as an analog value from the photodiode 2 to a digital value, a count adjustment circuit 5 (adjustment circuit) that performs adjustment such that a digital output value (ADCOUT1) from the analog-digital conversion circuit 4 changes in accordance with each value of a distance at least in a prescribed range of the distance between the photodiode 2 and a detected object (the finger in the drawing), a digital filter 6 for detecting a cycle of the digital output value (ADCOUT1) from the analog-digital conversion circuit 4, and an analog-digital conversion circuit 7 for converting an input current as an analog value from a photodiode 3 to a digital value.

Figure 15:
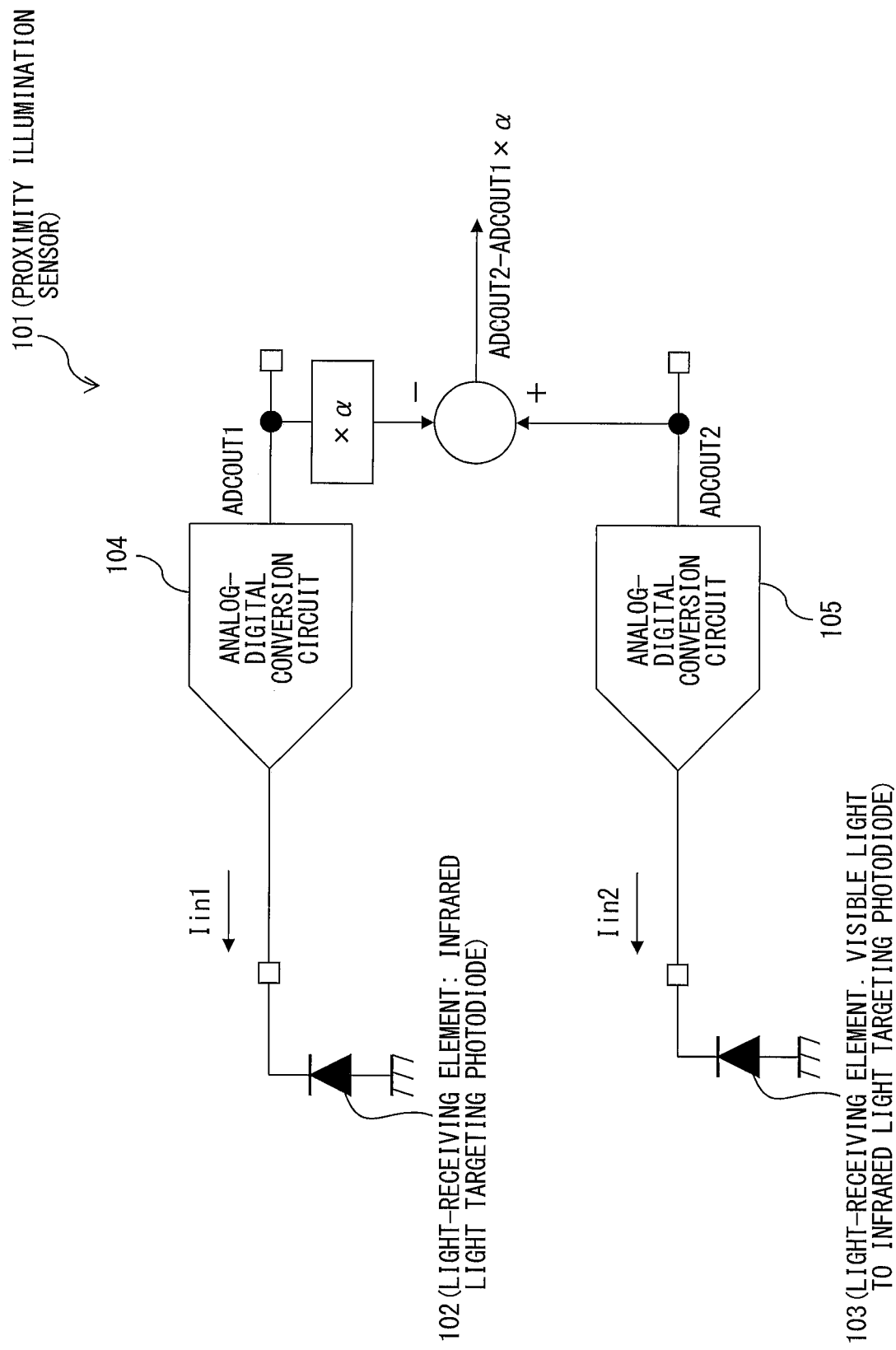
FIG. 15 illustrates one example of a proximity illumination sensor in related art that is installed in a portable device such as a cellular phone or a smart phone.
Figure 16:
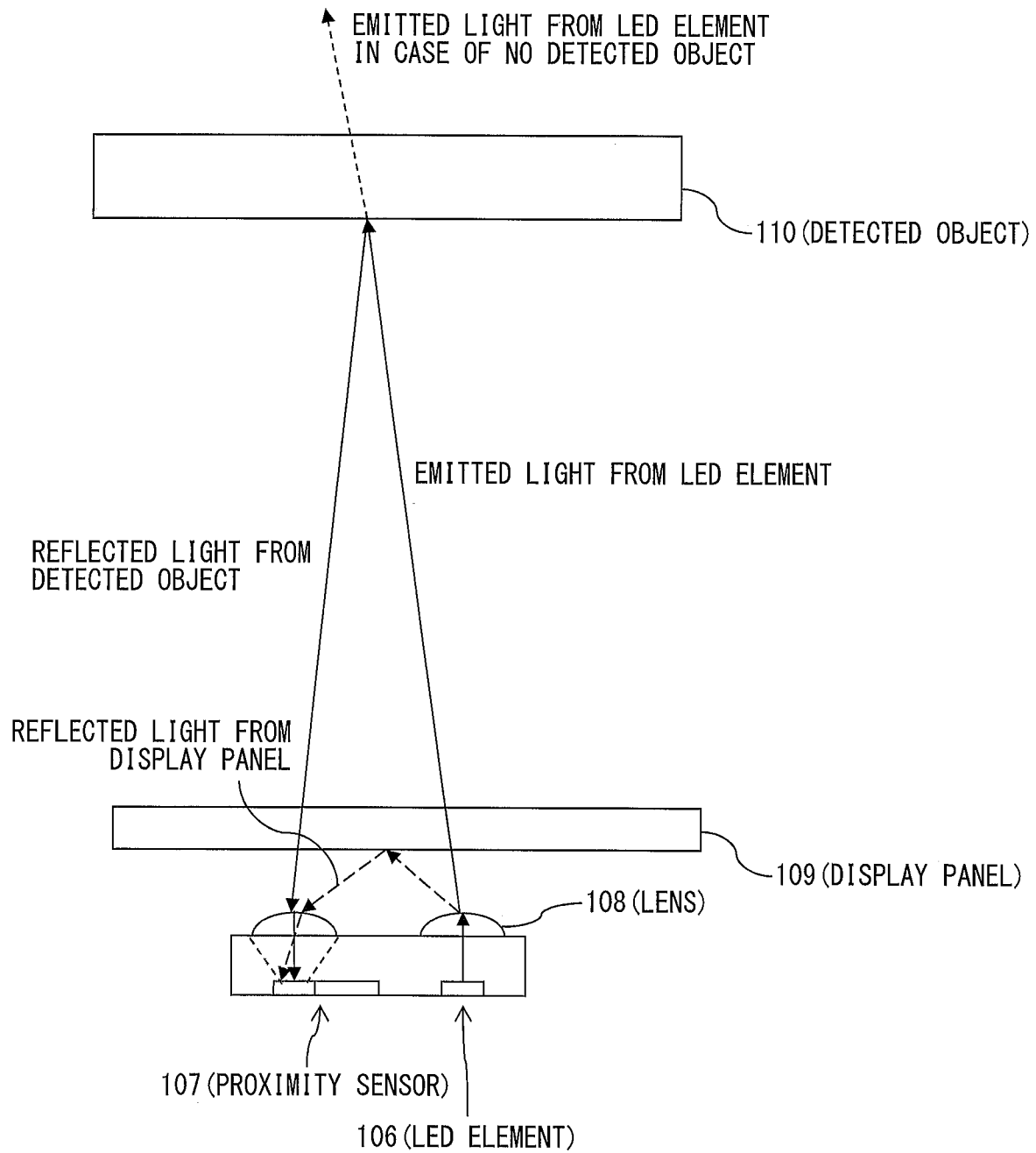
FIG. 16 illustrates one example of a proximity sensor in related art that is installed in a portable device such as a cellular phone or a smart phone.
Figure 17:
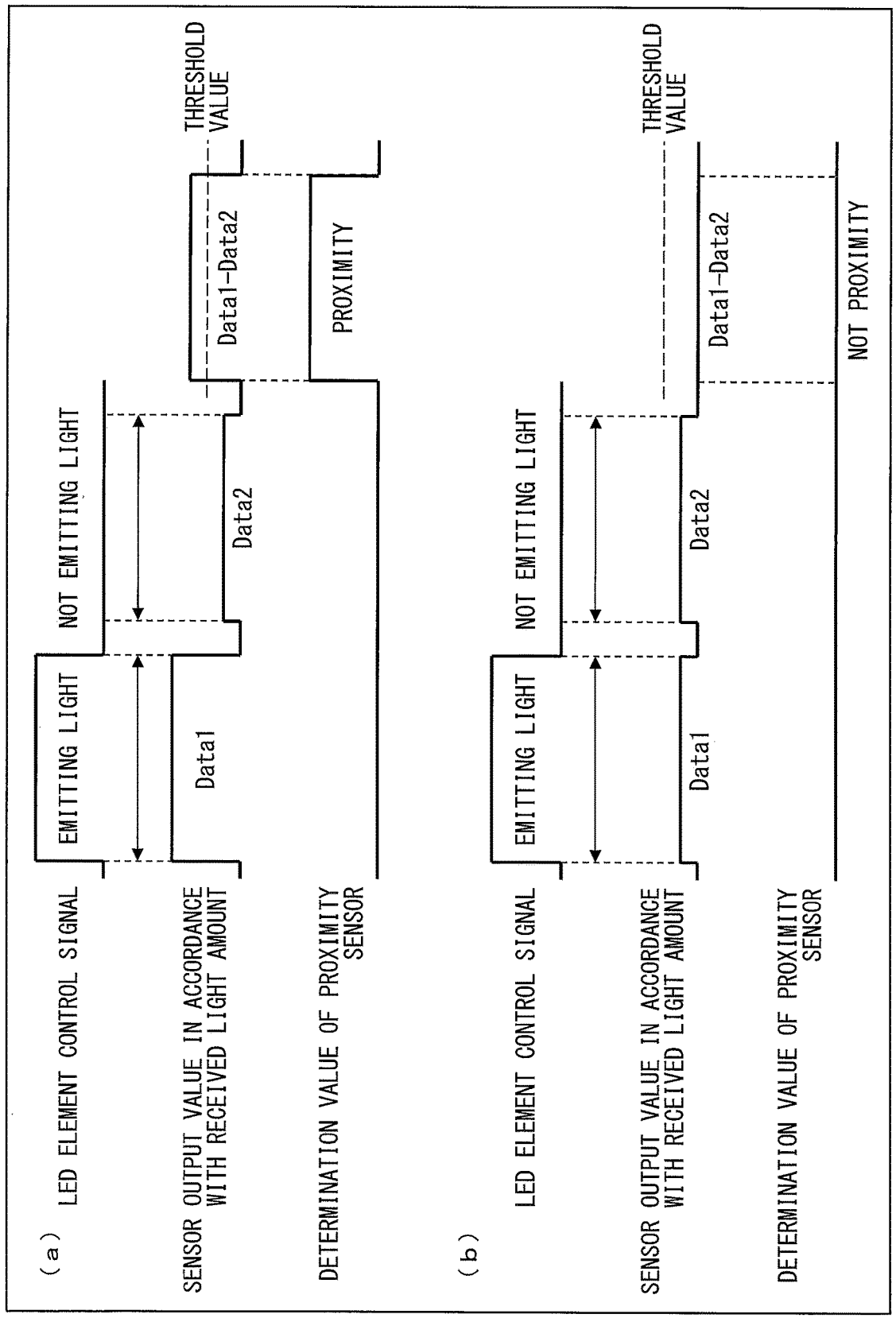
FIG. 17 illustrates examples of control signals of an LED element and output values and determination values of the proximity sensor, which are illustrated in FIG. 16.

A function as a proximity sensor and a function as an illumination sensor in the proximity illumination sensor 8 that includes the pulse detection function are the same as above description made by using FIG. 15, FIG. 16, and FIG. 17. Thus, descriptions thereof will not be made, and a description will be made with a focus on the pulse detection function.
(Integrating Type Analog-Digital Conversion Circuit and Count Adjustment Circuit)

Figure 2:
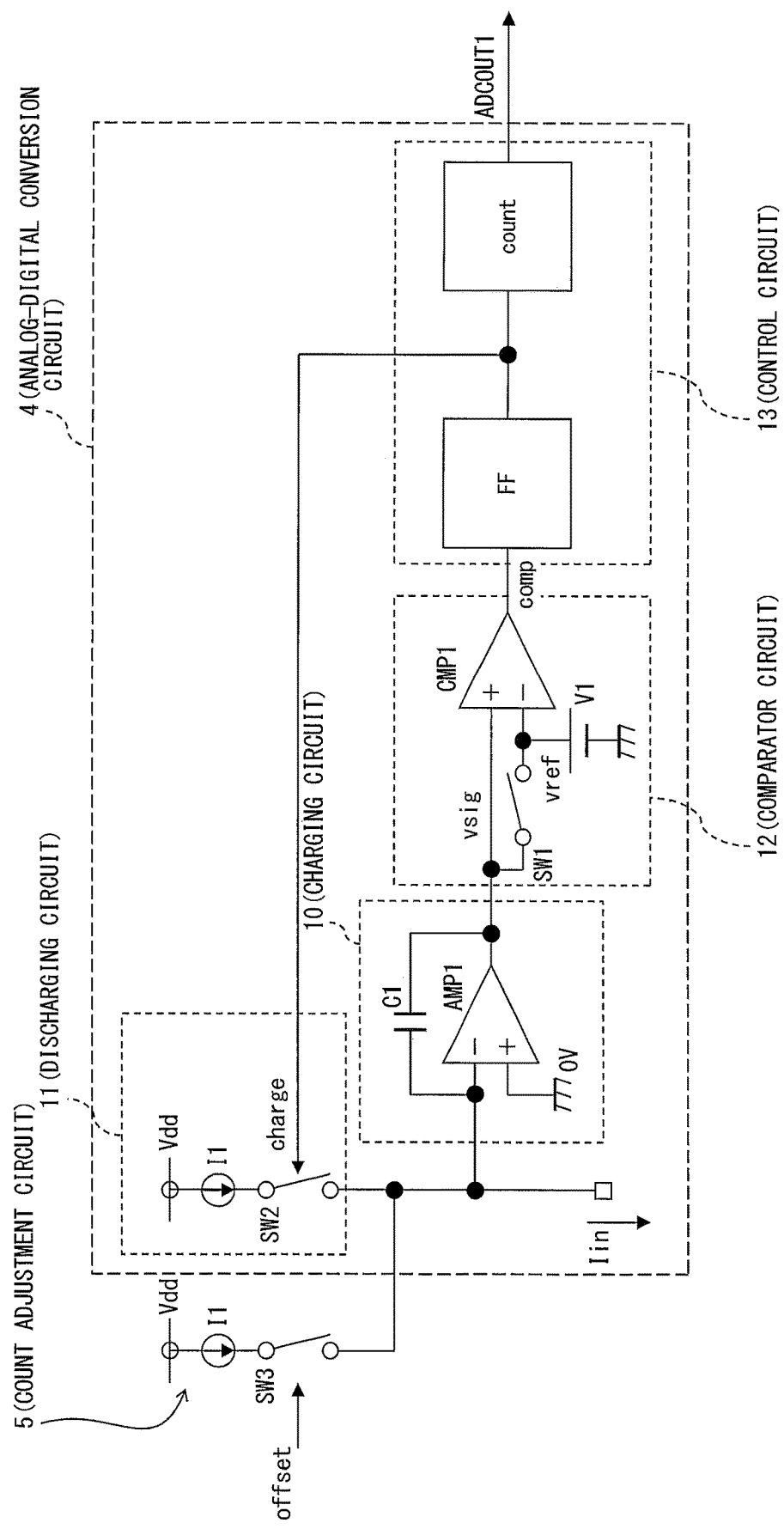
FIG. 2 is a diagram that illustrates a schematic configuration of an integrating type analog-digital conversion circuit and a count adjustment circuit which are included in the proximity illumination sensor which includes the pulse detection function.

FIG. 2 is a diagram that illustrates a schematic configuration of an integrating type analog-digital conversion circuit and a count adjustment circuit.

As illustrated in the drawing, the integrating type analog-digital conversion circuit 4 (hereinafter referred to as analog-digital conversion circuit 4) is an analog-digital conversion circuit that performs digital conversion of a current amount of the input current, outputs that, and includes a charging circuit 10, a discharging circuit 11, a comparator circuit 12, and a control circuit 13.

The charging circuit 10 includes a capacity (C1) that stores the charge which corresponds to an input current (Iin) from the photodiode 2 (not illustrated) and an operational amplifier (AMP1).

The discharging circuit 11 is a circuit that discharges a predetermined charge amount at a time via a switch 2 (SW2).

The comparator circuit 12 includes a comparator (CMP1) that compares an output voltage (vsig) of the charging circuit 10 with a reference voltage (vref) whose voltage is V1 and a switch 1 (SW1) that performs opening or closing between the reference voltage (vref) and the output of the charging circuit 10.

The control circuit 13 includes a flip-flop (FF) and a counter (count) and outputs the digital value that corresponds to the discharge frequency of the discharging circuit 11 as the output value (ADCOUT1).

Further, the count adjustment circuit 5 is formed with a similar configuration to the discharging circuit 11 and is a circuit that discharges a predetermined charge amount in a measurement period via a switch 3 (SW3). The discharge frequency is decided by the value of an offset (offset). That is, the switch 3 (SW3) is at a Hi voltage in accordance with the frequency that corresponds to the charge set by the offset, the switch 3 (SW3) is closed in a case of the Hi voltage, and discharge is performed.

Figure 3:
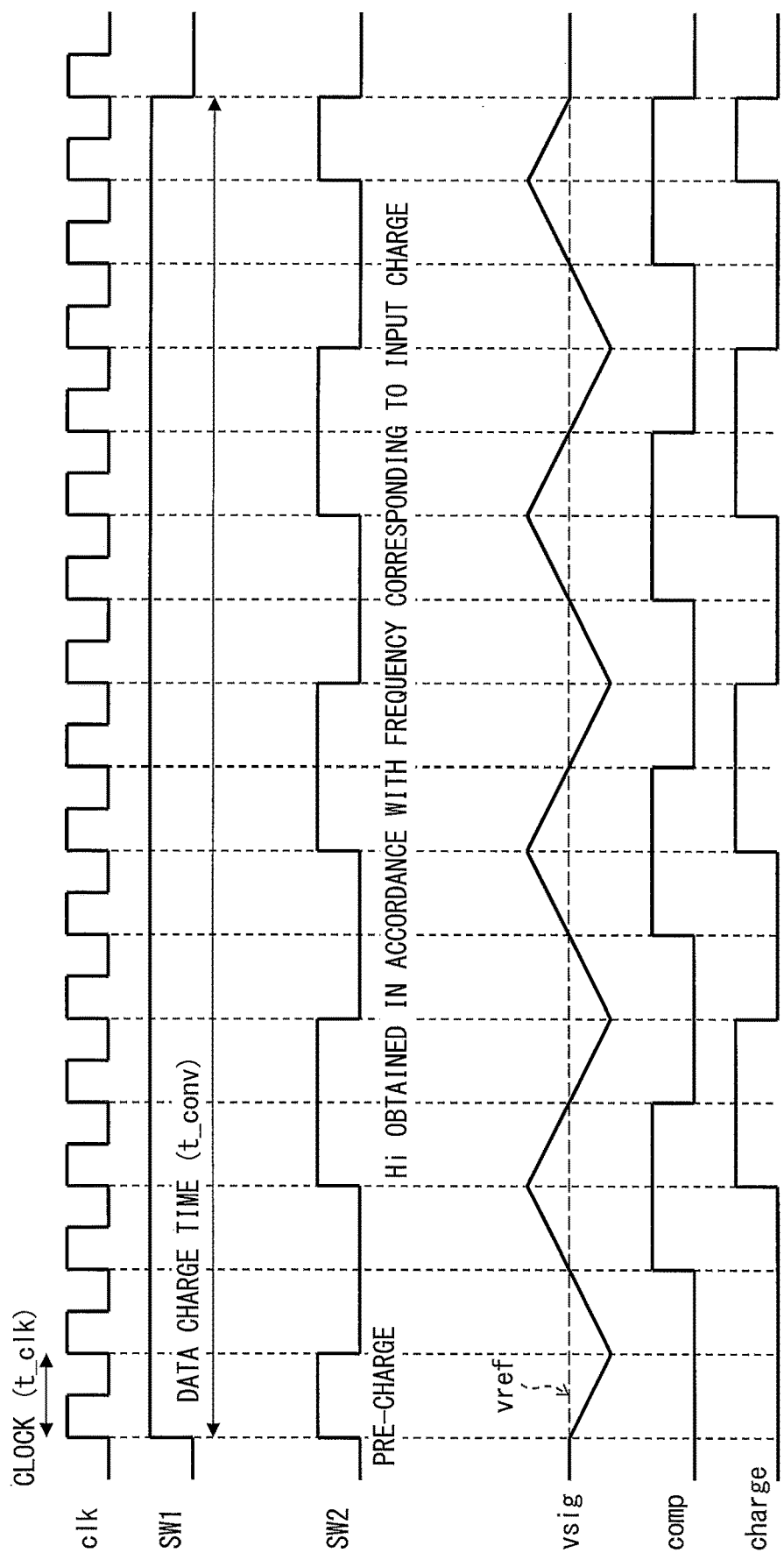
FIG. 3 illustrates one example of a drive signal of the analog-digital conversion circuit illustrated in FIG. 2.

FIG. 3 illustrates one example of a drive signal of the analog-digital conversion circuit 4 illustrated in FIG. 2.

Because the switch 1 (SW1) in the comparator circuit 12 is first closed, the output voltage (vsig) of the charging circuit 10 is charged to the reference voltage (vref). Then, in a data charge period (t_conv), the switch 1 (SW1) opens, the input current (Iin) from the photodiode 2 (not illustrated) is thereby charged in the capacity (C1) of the charging circuit 10, and the analog-digital conversion is performed.

A pre-charge operation for discharging a specific charge (I1×clock (t_clk)) is first performed by the discharging circuit 11, and the output voltage (vsig) of the charging circuit 10 lowers. Subsequently, the charging circuit 10 is charged by the input current (Iin) from the photodiode 2. When the output voltage (vsig) of the charging circuit 10 exceeds the reference voltage (vref), an output value (comp) of the comparator circuit 12 becomes the Hi voltage. A control signal (charge) that controls the switch 2 (SW2) of the discharging circuit 11 is output from the control circuit 13 one clock (t_clk) after the output value (comp) of the comparator circuit 12 becomes the Hi voltage. Then, the switch 2 (SW2) of the discharging circuit 11 is closed when the control signal (charge) is the Hi voltage, and the specific charge (I1×clock (t_clk)) is discharged from the discharging circuit 11. Subsequently, the discharge time that corresponds to a Hi voltage period of the control signal (charge) is counted by the counter (count) of the control circuit 13, and the value that corresponds to the charge amount input from the photodiode 2 may thereby be output as the digital output value (ADCOUT1).

An operation is performed such that the charge amount that is charged by the input current (Iin) from the photodiode 2 is equivalent to the charge amount that is discharged by I1×clock (t_clk).

In a case where the clock is set as t_clk, a data charge time is set as t_conv, a value obtained by counting the discharge time is set as count, and a reference current amount is set as I1, a charged charge amount=Iin×t_conv and a discharged charge amount=I1×t_clk×count are obtained. Then, based on the relationship of the charged charge amount=the discharged charge amount, count=(Iin×t_conv)/(I1×t_clk) holds. Here, the minimum resolution is decided by (I1×t_clk). In a case where charge is performed in the data charge time t_conv that is set as a period of t_clk×$2^n$ (n is the resolution), count=Iin/I1×$2^n$ is obtained.

For example, in a case of the resolution n=16 bits, a count number (count) is output in the range of 0 to 65535 in accordance with the value that corresponds to the input current Iin. Accordingly, such an analog-digital conversion circuit 4 is included, and the analog-digital conversion with a wide dynamic range and high resolution is thereby enabled.

The proximity illumination sensor 8 illustrated in FIG. 1 includes the analog-digital conversion circuit 4, which is the analog-digital conversion circuit of the integrating type, and may thus realize the proximity illumination sensor 8 that is capable of the analog-digital conversion with a wide dynamic range and high resolution.

Further, the analog-digital conversion circuit 4 of the proximity illumination sensor 8 includes a count adjustment circuit 5 (adjustment circuit) so that a fluctuation in the cycle of the pulse may easily be detected. As illustrated in FIG. 2, the count adjustment circuit 5 is a circuit that discharges a predetermined charge amount in the measurement period via the switch 3 (SW3) and may adjust the count of the output value (ADCOUT1) from the analog-digital conversion circuit 4 because the discharge frequency is decided by the value of the offset (offset).

As described above, in a case where the count adjustment circuit 5 is used and where the offset is set as the count number to be adjusted, the charged charge amount=Iin×t_conv and the discharged charge amount=I1×t_clk×count+I1×t_clk×offset are obtained.

Based on the relationship of the charged charge amount=the discharged charge amount, count=(Iin×t_conv)/(I1×t_clk)−offset holds. Here, in a case where charge is performed in the data charge time t_conv that is set as the period of t_clk×$2^n$ (n is the resolution), count=Iin×$2^n$−offset is obtained, and the count may be shifted by the offset for the count number that is requested for the adjustment. Accordingly, the count adjustment circuit 5 is used, and the adjustment may thereby be performed such that the output value (ADCOUT1) from the analog-digital conversion circuit 4 changes in accordance with each value of the distance at least in a prescribed range of the distance between the photodiode 2 and the detected object.

Figure 4:
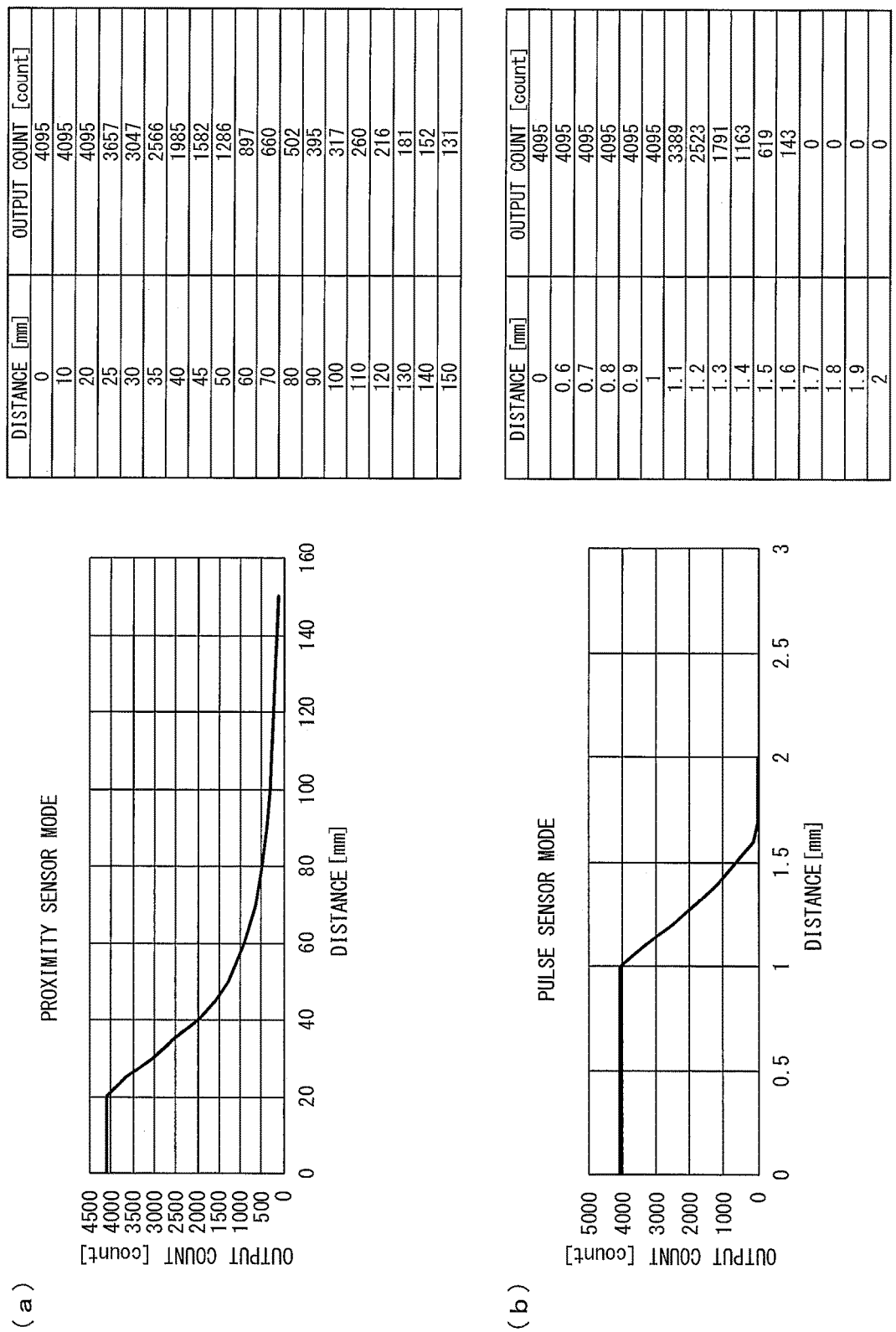
FIG. 4 is a diagram that illustrates an output value from the analog-digital conversion circuit in a case where the proximity illumination sensor which includes the pulse detection function is used in a proximity sensor mode and a case where the proximity illumination sensor is used in a pulse sensor mode.

FIG. 4 is a diagram that illustrates the output value (ADCOUT1) from the analog-digital conversion circuit 4 which changes in accordance with the distance between the photodiode 2 and the detected object in a case where the proximity illumination sensor 8 which includes the pulse detection function is used in the proximity sensor mode and a case where the proximity illumination sensor 8 is used in the pulse sensor mode.

FIG. 4(a) is the case where the proximity illumination sensor 8 is used in the proximity sensor mode. Because a purpose of the proximity sensor mode is to perform detection with respect to the detected object in a distance of about 100 mm, an output count which is the output value from the analog-digital conversion circuit 4 is saturated in a close distance of 20 mm or less in a case where the finger approaches, for example.

As already described above, in the proximity sensor mode, a determination is made only whether or not the detected object is present close to the photodiode 2. Thus, even in a case where the output value of the analog-digital conversion circuit 4 is saturated, the proximity determination about the detected object is not largely influenced.

However, in a case where the pulse of the user is measured, because the measurement is performed by causing the finger of the user to approach the photodiode 2, a configuration has to be made such that the output value of the analog-digital conversion circuit 4 is not saturated in a close distance of about 1 to 2 mm such as placement of the finger. In such a close distance of about 1 to 2 mm, the output value of the analog-digital conversion circuit 4 is saturated in general. However, in the proximity illumination sensor 8, the count adjustment circuit 5 is used to perform the adjustment such that the output value of the analog-digital conversion circuit 4 is not saturated in at least a prescribed range of the distance between the photodiode 2 and the detected object (for example, a close distance of about 1 to 1.6 mm such as placement of the finger).

FIG. 4(b) is the case where the proximity illumination sensor 8 is used in the pulse sensor mode. In the pulse sensor mode, the output value of the analog-digital conversion circuit 4 is not saturated in a close distance of about 1 to 1.6 mm such as placement of the finger. Thus, pulse measurement is enabled.

Here, a description will be made about a reason why the detection of the pulse of the user is difficult in a case where the output value of the analog-digital conversion circuit 4 is saturated. In a case where a digital filter process, which will be described later, is performed for the saturated output value from the analog-digital conversion circuit 4, a state where the fluctuation in the count due to the pulse is not present, that is, a state where the output value is fixed to a saturated value occurs, and the output value resulting from the digital filter process becomes zero and does not fluctuate. Thus, the detection of the pulse of the user is difficult.

On the other hand, in a case where the digital filter process is performed for the output value, which is not saturated, from the analog-digital conversion circuit 4, a state where the fluctuation in the count due to the pulse is present is obtained, and the output value resulting from the digital filter process may thereby be recognized as the fluctuation in the cycle of the pulse.

Further, a description will be made about a reason why the count adjustment circuit 5 is used to perform the adjustment such that the output value of the analog-digital conversion circuit 4 is not saturated in at least a prescribed range of the distance between the photodiode 2 and the detected object (for example, a close distance of about 1 to 1.6 mm such as placement of the finger) and the proximity illumination sensor 8 may thereby be used in the pulse sensor mode.

In a case where the proximity illumination sensor 8 is mounted on a portable device such as a smart phone, the photodiode 2 is in general provided in a lower portion of a display panel or an internal portion of the display panel. Accordingly, a gap is present between the photodiode 2 and a surface (a contact surface with the finger of the user) of the display panel. Thus, even in a state where the finger of the user completely contacts with the display panel, a distance of about 1 to 1.6 mm usually remains.

From such a reason, in the proximity illumination sensor 8, the count adjustment circuit 5 is used to perform the adjustment such that the output value of the analog-digital conversion circuit 4 is not saturated in at least a prescribed range of the distance between the photodiode 2 and the detected object (for example, a close distance of about 1 to 1.6 mm such as placement of the finger), and the proximity illumination sensor 8 is thereby used in the pulse sensor mode.

Because the gap between the photodiode 2 and the surface (the contact surface with the finger of the user) of the display panel may be different in accordance with kinds or the like of portable devices, the count adjustment circuit 5 is used to perform optimal adjustment such that the output value of the analog-digital conversion circuit 4 is not saturated in at least a prescribed range of the distance between the photodiode 2 and the detected object, and the state where the fluctuation in the count due to the pulse is present has to be thereby obtained.

(Light-Receiving Element)

Figure 5:
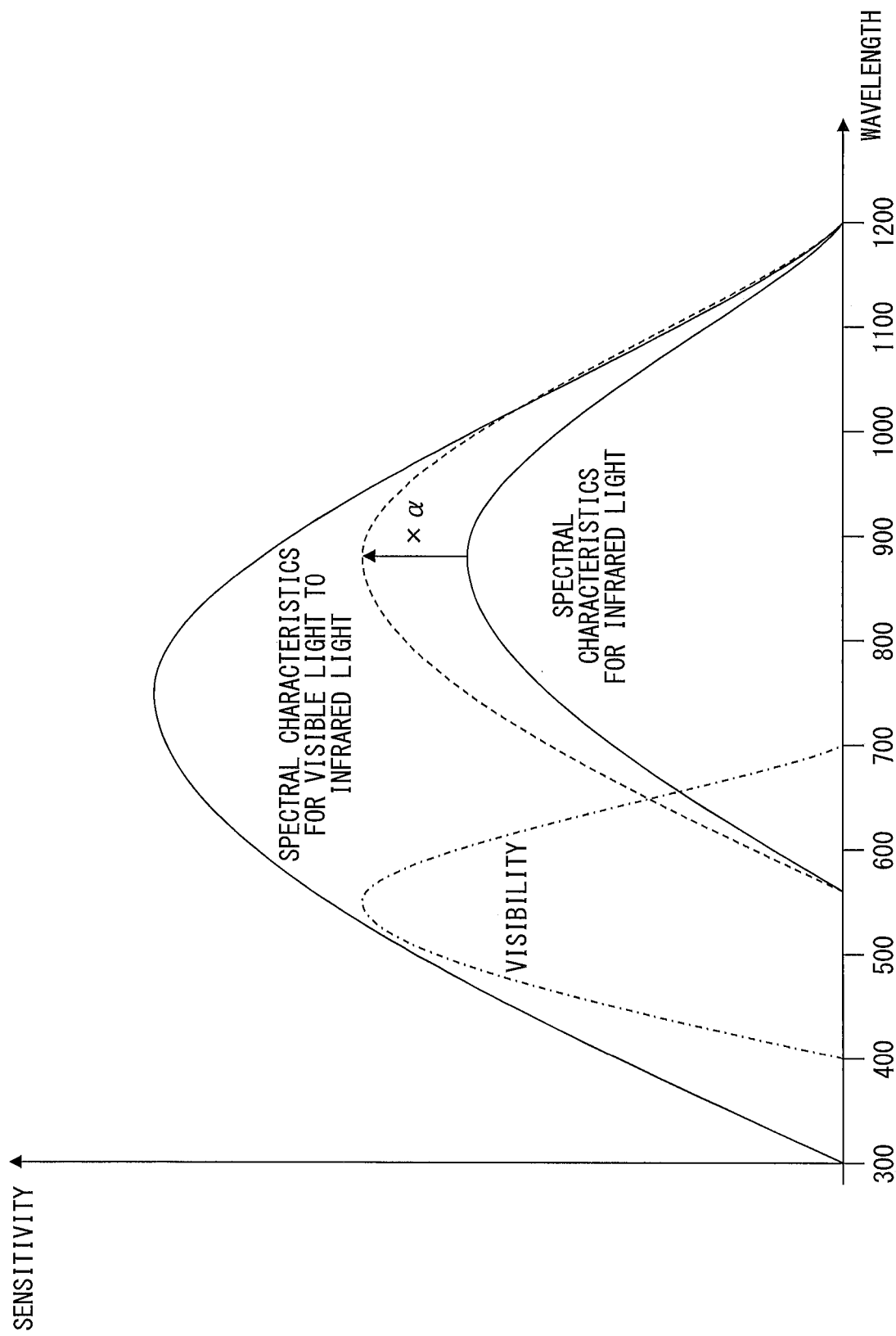
FIG. 5 is a diagram that illustrates examples of spectral characteristics of an infrared light targeting photodiode and a visible light to infrared light targeting photodiode which are included in the proximity illumination sensor.

FIG. 5 is a diagram that illustrates examples of spectral characteristics of the infrared light targeting photodiode 2 which has the spectral characteristics for the infrared light region and the visible light to infrared light targeting photodiode 3 which has the spectral characteristics for the region of visible light to infrared light, which are included in the proximity illumination sensor 8.

When the proximity illumination sensor 8 operates as the illumination sensor, the output of the spectral characteristics for the infrared light that is multiplied by α is subtracted from the output of the spectral characteristics for the visible light to the infrared light, and illumination characteristics that correspond to visibility may thereby be realized.

Further, when the proximity illumination sensor 8 operates as the proximity sensor, the output of the spectral characteristics for the infrared light is used, visible light may thereby be reduced, and noises such as a fluorescent light may be reduced.

In addition, when the proximity illumination sensor 8 operates as a pulse sensor, the output of the spectral characteristics for the infrared light is used, and the reflected light that is reflected by a fingertip of a person in accordance with the blood flow may thereby be detected. (Digital Filter)

Figure 6:
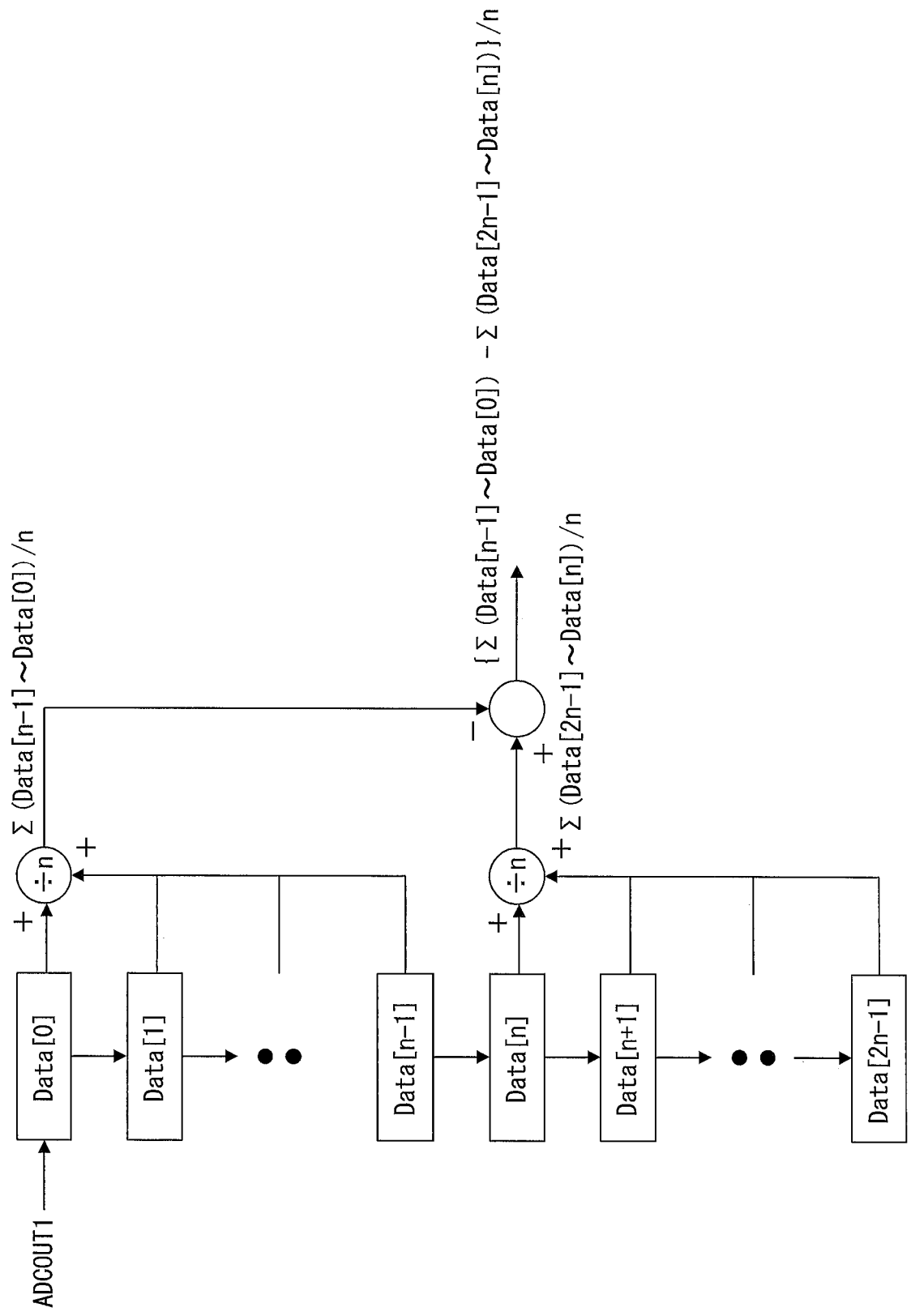
FIG. 6 is a diagram for explaining a digital filter that is included in the proximity illumination sensor.

FIG. 6 is a diagram for explaining a digital filter 6 that is included in the proximity illumination sensor 8.

As illustrated in the drawing, the digital filter 6 is a finite impulse response (FIR) filter and is configured with a low-pass filter and a high-pass filter.

The low-pass filter may be configured with moving average processing, and the high-pass filter may be configured with difference processing.

The characteristics of the low-pass filter and the high-pass filter may be obtained by retaining 2n sequential output values (ADCOUT1) of the analog-digital conversion circuit 4 and subtracting the average value of Data[n−1] to Data[0] from the average value of Data[2n−1] to Data[n].

n is the number of data to be retained and may adjust a passband of the digital filter 6. For example, in a case where the output value (ADCOUT1) of the analog-digital conversion circuit 4 is output for each 10 msec, setting of n=24, approximately, facilitates the detection of the cycle of the pulse of the user.

Figure 7:
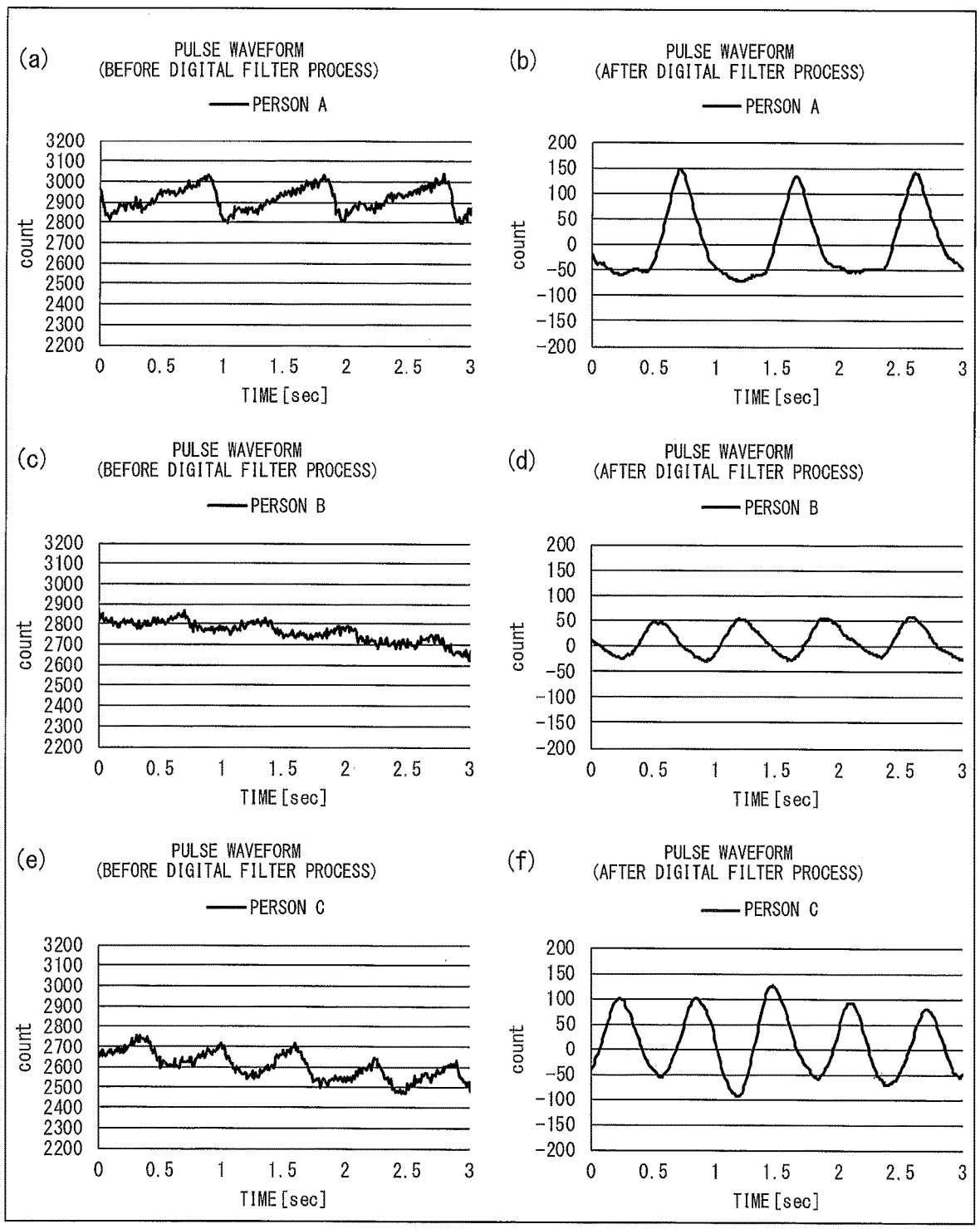
FIG. 7 is a diagram that illustrates pulse waveforms at times before and after the output values of the analog-digital conversion circuit are processed by using the digital filter in a case where the proximity illumination sensor is caused to operate as the pulse sensor.

FIG. 7 is a diagram that illustrates pulse waveforms at times before and after the output values (ADCOUT1) of the analog-digital conversion circuit 4 are processed by using the digital filter 6 in a case where the proximity illumination sensor 8 is caused to operate as the pulse sensor.

FIG. 7(a) and FIG. 7(b) illustrate pulse waveforms at times before and after a process of the digital filter 6 in a case of a user A (person A). FIG. 7(c) and FIG. 7(d) illustrate pulse waveforms at times before and after the process of the digital filter 6 in a case of a user B (person B). FIG. 7(e) and FIG. 7(f) illustrate pulse waveforms at times before and after the process of the digital filter 6 in a case of a user C (person C).

As illustrated in the drawing, there are differences in the pulse waveforms among the users. However, the digital filter 6 is used, and an effect of the low-pass filter of smoothing fine noises at high frequencies and an effect of the high-pass filter of removing differences (DC levels) of reflected light amounts due to the users may thereby be obtained. The pulse waveforms at times after the process of the digital filter 6 are obtained as pulse waveforms that have amplitudes with zero being the center, regardless of the users.

Accordingly, the maximum values and the minimum values of the pulse waveforms which are output from the digital filter 6 and illustrated in FIG. 7(b), FIG. 7(d), and FIG. 7(f) are detected, and the cycles of the pulses of the users may easily be detected.

Further, the points that the pulse waveforms, which are output from the digital filter 6 and illustrated in FIG. 7(b), FIG. 7(d), and FIG. 7(f), intersect zero are detected, that is, the cycles in which the pulse waveforms output from the digital filter 6 become zero are detected, and the cycles of the pulses of the users may thereby be detected easily.

In the above, a description is made about a case where the digital filter 6 is the finite impulse response (FIR) filter as an example. However, the digital filter 6 may be an infinite impulse response (IIR) filter.

Figure 8:
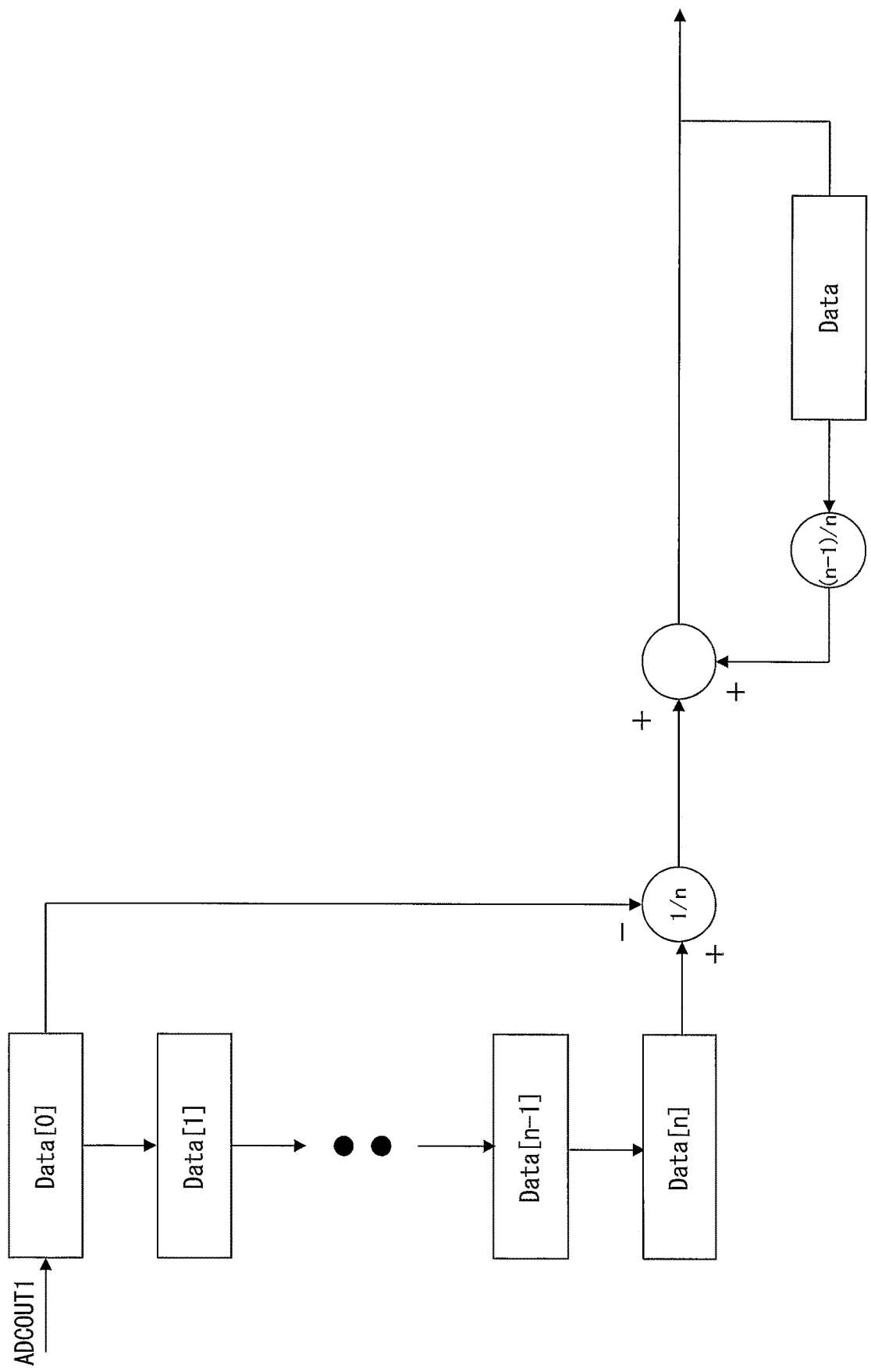
FIG. 8 is a diagram that illustrates one example of the digital filter which is configured with an infinite impulse response (IIR) filter.

FIG. 8 is a diagram that illustrates one example of the digital filter which is configured with the infinite impulse response (IIR) filter.

In a case where the digital filter that is configured with the infinite impulse response (IIR) filter illustrated in the drawing is used, this provides an advantage of enabling design of a digital filter that has high performance with less computation than the digital filter configured with the finite impulse response (FIR) filter. However, there are disadvantages of presence of a feedback path, instability due to high coefficient sensitivity, non-linear phase responses, and so forth.

Second Embodiment

A second embodiment of the present invention will next be described with reference to FIG. 9. In the above-described first embodiment, a description is made about the sensor apparatus that includes the proximity illumination sensor which includes the pulse detection function, as an example. However, this embodiment is different from the above first embodiment in a point that a description will be made about a sensor apparatus that includes a proximity sensor which includes the pulse detection function, as an example. The description in the first embodiment applies to the other configurations. For convenience of description, the same reference characters will be given to members that have the same functions as the members illustrated in the drawings associated with the first embodiment, and a description thereof will not be made.

Figure 9:
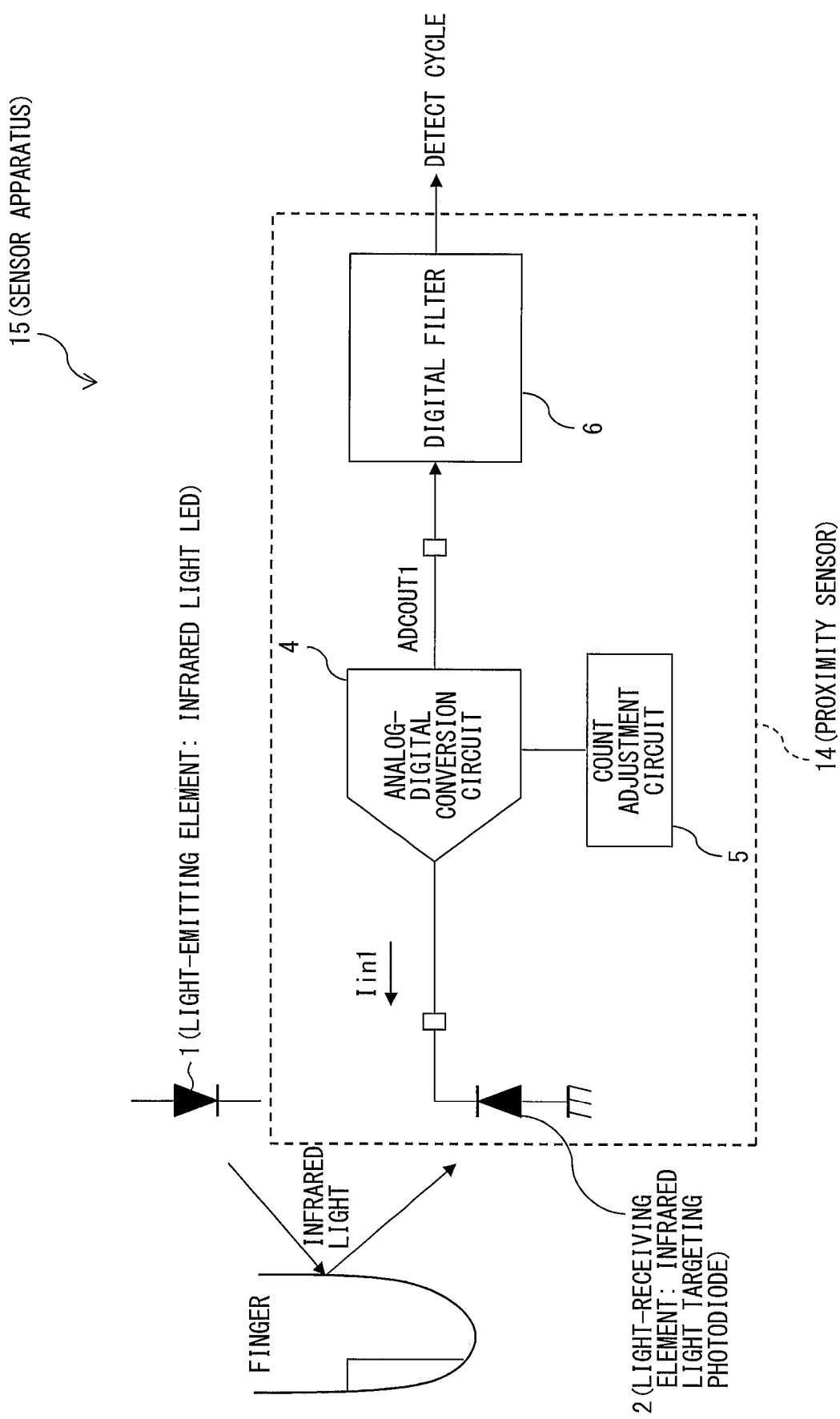
FIG. 9 is a diagram that illustrates a schematic configuration of a sensor apparatus that includes the infrared light LED as the light-emitting element and a proximity sensor which includes the pulse detection function.

FIG. 9 is a diagram that illustrates a schematic configuration of a sensor apparatus 15 that includes the infrared light LED 1 as the light-emitting element and a proximity sensor 14 which includes the pulse detection function.

As illustrated in the drawing, the proximity sensor 14 that includes the pulse detection function includes the infrared light targeting photodiode 2 that has the spectral characteristics for the infrared light region, the analog-digital conversion circuit 4 for converting the input current (Iin1) as an analog value from the photodiode 2 to a digital value, the count adjustment circuit 5 (adjustment circuit) that performs adjustment such that the digital output value (ADCOUT1) from the analog-digital conversion circuit 4 changes in accordance with each value of the distance at least in a prescribed range of the distance between the photodiode 2 and the detected object (the finger in the drawing), and the digital filter 6 for detecting the cycle of the digital output value (ADCOUT1) from the analog-digital conversion circuit 4.

Such a proximity sensor 14 that includes the pulse detection function is capable of detecting the pulse of the user by using the proximity sensor.

A detection method of the pulse in the proximity sensor 14 that includes the pulse detection function has already been described in the above-described first embodiment. The function as the proximity sensor has already been described with reference to FIG. 16 and FIG. 17. Thus, descriptions thereof will not be made here.

Third Embodiment

A third embodiment of the present invention will next be described with reference to FIG. 10. In the above-described first and second embodiments, descriptions are made about cases where the digital filter 6 that performs the digital filter process for the digital output values (ADCOUT1) from the analog-digital conversion circuit 4 is included in the proximity illumination sensor which includes the pulse detection function and in the proximity sensor which includes the pulse detection function, as examples. However, this embodiment is different from the above first and second embodiments in a point that the digital filter process for the digital output values (ADCOUT1) from the analog-digital conversion circuit 4 is processed in a software manner outside of the proximity illumination sensor or the proximity sensor. The descriptions in the first and second embodiments apply to the other configurations. For convenience of description, the same reference characters will be given to members that have the same functions as the members illustrated in the drawings associated with the above first and second embodiments, and a description thereof will not be made.

Figure 10:
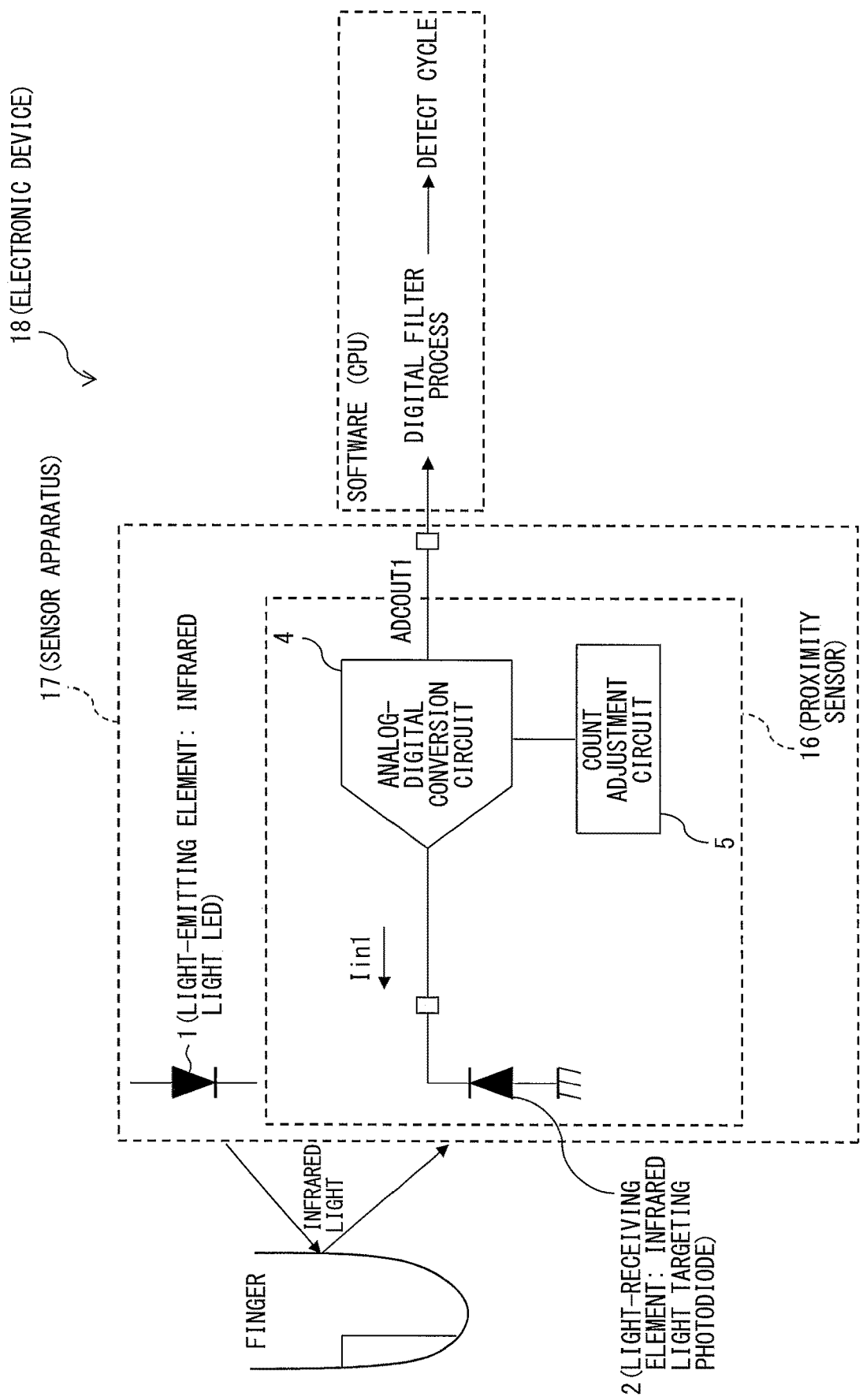
FIG. 10 is a diagram that illustrates a schematic configuration of an electronic device that includes the infrared light LED as the light-emitting element, a proximity sensor, and a CPU which performs a digital filter process.

FIG. 10 is a diagram that illustrates a schematic configuration of an electronic device 18 that includes the infrared light LED 1 as the light-emitting element, a proximity sensor 16, and a CPU.

As illustrated in the drawing, the proximity sensor 16 includes the infrared light targeting photodiode 2 that has the spectral characteristics for the infrared light region, the analog-digital conversion circuit 4 for converting the input current (Iin1) as an analog value from the photodiode 2 to a digital value, and the count adjustment circuit 5 (adjustment circuit) that performs adjustment such that the digital output value (ADCOUT1) from the analog-digital conversion circuit 4 changes in accordance with each value of the distance at least in a prescribed range of the distance between the photodiode 2 and the detected object (the finger in the drawing).

Further, the digital filter process for detecting the cycle of the digital output values (ADCOUT1) from the analog-digital conversion circuit 4 is performed in a software manner in the CPU of the electronic device 18.

It is sufficient that the electronic device 18 has a processing unit such as a CPU that is capable of performing the digital filter process. Examples may include a cellular phone, a smart phone, a digital camera, and so forth.

The electronic device in such a configuration is capable of detecting the pulse of the user by using the proximity illumination sensor or the proximity sensor. The digital filter process is processed by software, and a configuration up to the analog-digital conversion circuit may thereby be sufficient as the proximity illumination sensor or the proximity sensor. This results in a simple configuration, and a low price may be realized.

Fourth Embodiment

A fourth embodiment of the present invention will next be described with reference to FIG. 11 and FIG. 12. In the above-described first to third embodiments, descriptions are made about cases where the infrared light targeting photodiode that has the spectral characteristics for the infrared light region and the visible light to infrared light targeting photodiode that has spectral characteristics for the region of visible light to infrared light are included as the light-receiving elements, as examples. However, this embodiment is different from the above first to third embodiments in a point that a spectral characteristic changeable light-receiving element is included. The descriptions in the first to third embodiments apply to the other configurations. For convenience of description, the same reference characters will be given to members that have the same functions as the members illustrated in the drawings associated with the above first to third embodiments, and a description thereof will not be made.

Figure 11:
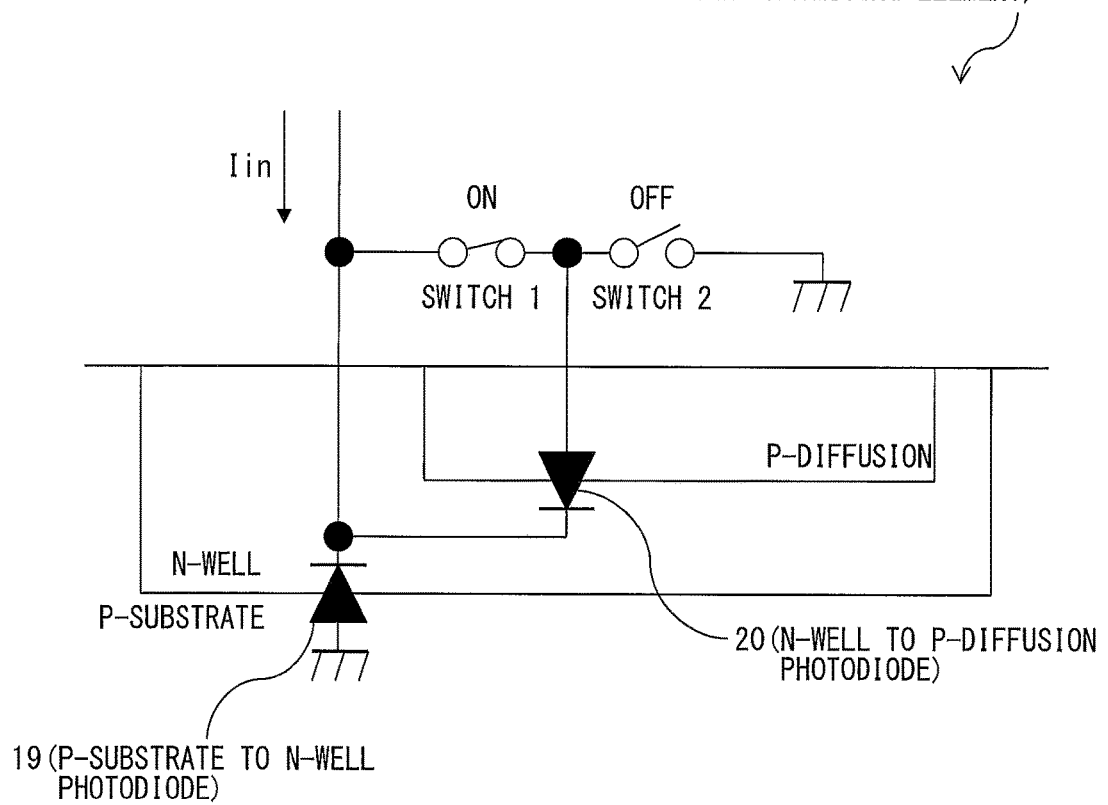
FIG. 11 is a diagram that illustrates a schematic configuration of a spectral characteristic changeable light-receiving element.

FIG. 11 is a diagram that illustrates a schematic configuration of a spectral characteristic changeable light-receiving element 21.

As illustrated in the drawing, the spectral characteristic changeable light-receiving element 21 is a light-receiving element that includes two or more p-n junctions. Further, a structure of the spectral characteristic changeable light-receiving element 21 is configured with a p-substrate, an n-well, and a p-diffusion in the lamination order, and the spectral characteristics may be changed by a switch 1 and a switch 2.

That is, the spectral characteristic changeable light-receiving element 21 includes a p-substrate to n-well photodiode 19 that has the spectral characteristics for the infrared light region and an n-well to p-diffusion photodiode 20 that has the spectral characteristics for a visible light region.

Then, in a case where the switch 1 in the spectral characteristic changeable light-receiving element 21 is ON and the switch 2 is OFF, the p-substrate to n-well photodiode 19 is used, and the n-well to p-diffusion photodiode 20 is short-circuited. Accordingly, the spectral characteristic changeable light-receiving element 21 has the spectral characteristics for the infrared light region.

On the other hand, in a case where the switch 1 in the spectral characteristic changeable light-receiving element 21 is OFF and the switch 2 is ON, the p-substrate to n-well photodiode 19 is used, and the n-well to p-diffusion photodiode 20 is also used. Accordingly, the spectral characteristic changeable light-receiving element 21 has the spectral characteristics for the region of visible light to infrared light.

Figure 12:
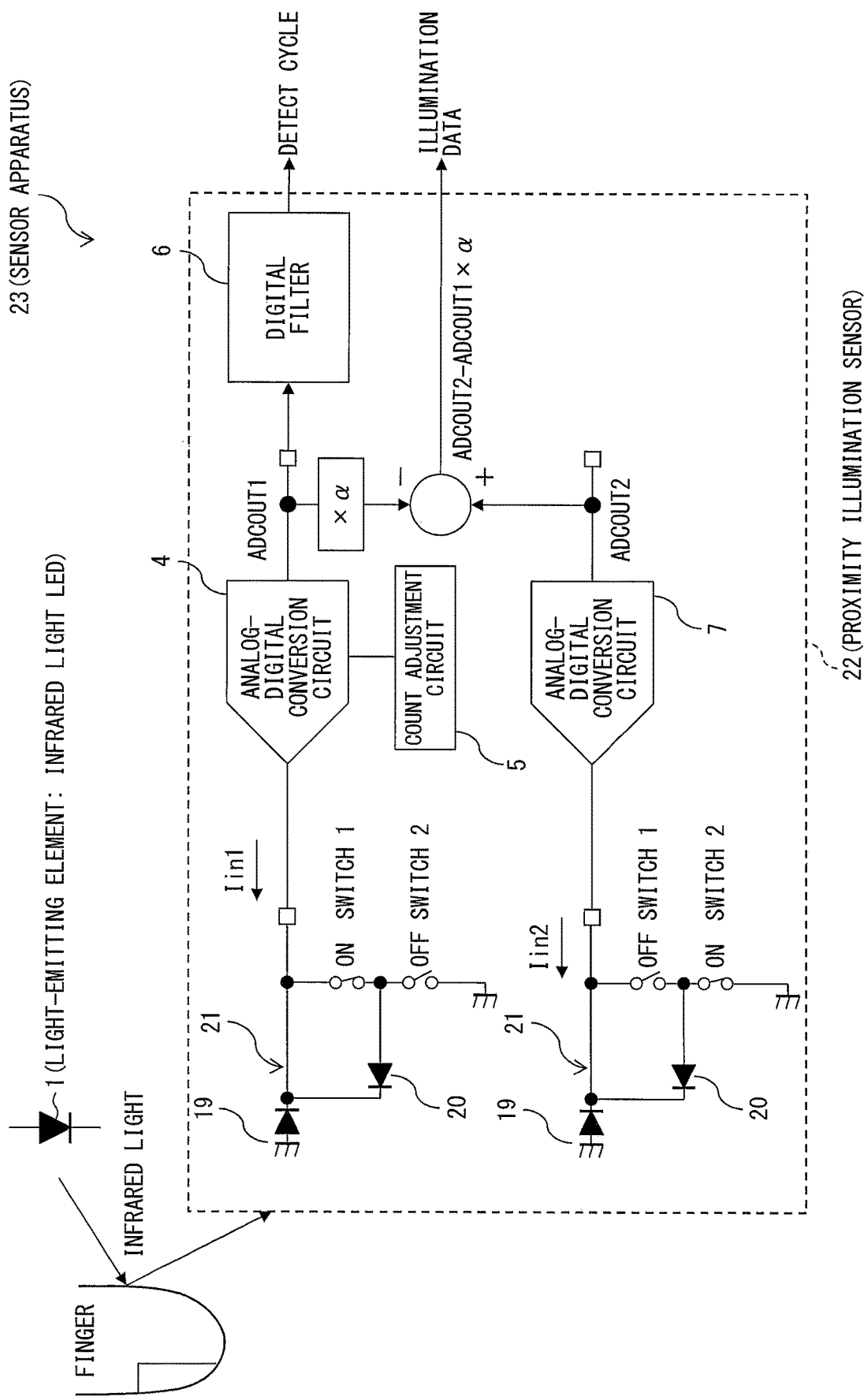
FIG. 12 is a diagram that illustrates a schematic configuration of a sensor apparatus that includes the infrared light LED as the light-emitting element and a proximity illumination sensor which has two spectral characteristic changeable light-receiving elements and includes the pulse detection function.

FIG. 12 is a diagram that illustrates a schematic configuration of a sensor apparatus 23 that includes the infrared light LED 1 as the light-emitting element and a proximity illumination sensor 22 which has two spectral characteristic changeable light-receiving elements 21 and includes the pulse detection function.

As illustrated in the drawing, the proximity illumination sensor 22 that includes the pulse detection function uses the spectral characteristic changeable light-receiving element 21, in which the switch 1 is turned ON and the switch 2 is turned OFF, as the infrared light targeting photodiode that has the spectral characteristics for the infrared light region and uses the spectral characteristic changeable light-receiving element 21, in which the switch 1 is turned OFF and the switch 2 is turned ON, as the visible light to infrared light targeting photodiode that has the spectral characteristics for the region of visible light to infrared light.

In the above configuration, the spectral characteristic changeable light-receiving element 21 which has the same structure and in which only connection states of the switches are different may be used. Accordingly, the light-receiving element may more efficiently be formed than forming two light-receiving elements that have different structures.

Fifth Embodiment

A fifth embodiment of the present invention will next be described with reference to FIG. 13. In the above-described first to fourth embodiments, descriptions are made about cases where a light-receiving unit (light-receiving surface) of the light-receiving element is formed in a flush manner, as examples. However, this embodiment is different from the above first to fourth embodiments in a point that the light-receiving unit (light-receiving surface) of the light-receiving element is divided into plural portions. The descriptions in the first to fourth embodiments apply to the other configurations. For convenience of description, the same reference characters will be given to members that have the same functions as the members illustrated in the drawings associated with the above first to fourth embodiments, and a description thereof will not be made.

Figure 13:
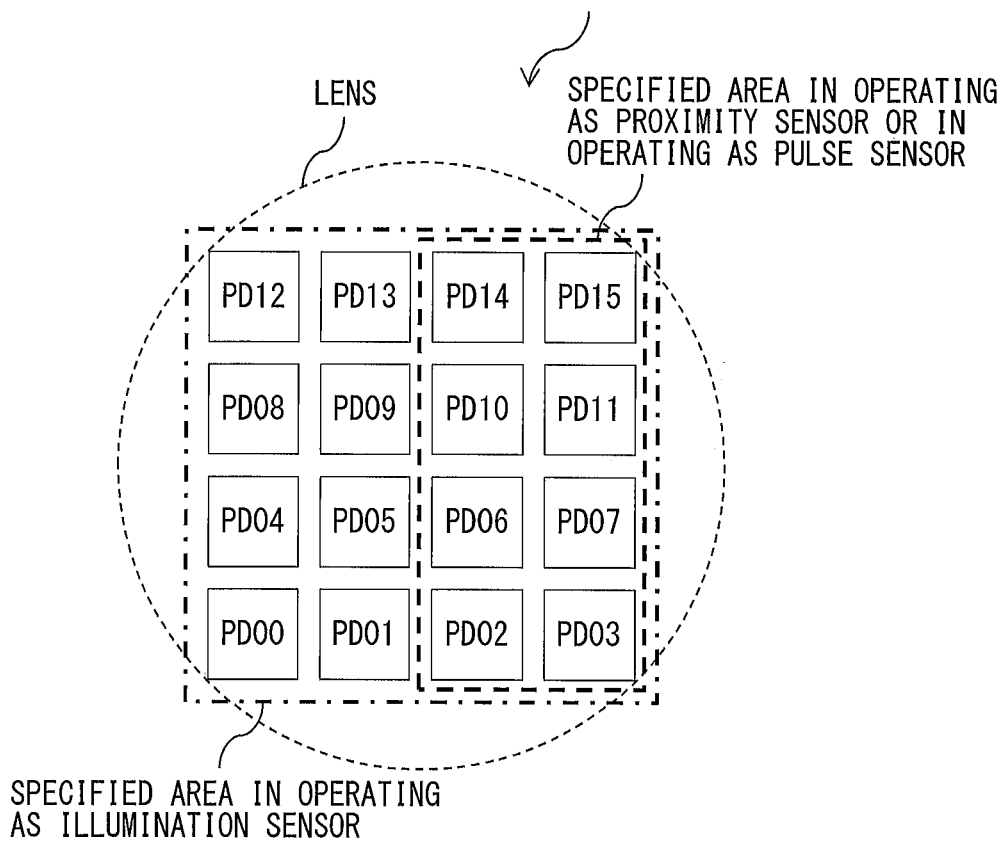
FIG. 13 is a diagram that illustrates a schematic configuration of a light-receiving element in which a light-receiving unit (light-receiving surface) is divided into plural portions.

FIG. 13 is a diagram that illustrates a schematic configuration of a light-receiving element 24 in which the light-receiving unit (light-receiving surface) is divided into plural portions.

As illustrated in the drawing, the light-receiving element 24 has the light-receiving unit (light-receiving surface) that is divided into plural portions. In this embodiment, the light-receiving unit (light-receiving surface) that is divided into 16 portions in a matrix manner is used. However, the number of divisions or the shapes of divisions are not particularly limited.

Further, in operating as the illumination sensor, the whole light-receiving unit (light-receiving surface), that is, all light-receiving surfaces PD00 to PD15 resulting from the division into 16 portions are used. This is because in operating as the illumination sensor, a light-receiving area of the light-receiving element is preferably used largely in order to enhance the sensitivity at low illumination and to improve directional characteristics.

Meanwhile, as illustrated in FIG. 16, a spot of reflected light that is emitted from the LED element 106 and reflected by the display panel 109 usually tends to be offset to the opposite side from the LED element 106. Thus, in operating as the proximity sensor, in a case where the light-emitting element is present on the left side of the FIG. 13, the light-receiving surfaces PD02, PD03, PD06, PD07, PD10, PD11, PD14, and PD15 among the light-receiving surfaces PD00 to PD15 resulting from the division into 16 portions are preferably selected as the light-receiving areas (specified areas). Accordingly, the noise light amount due to reflected light from the display panel in a portable device or the like may be reduced.

Also in operating as the pulse sensor, similarly to a case of operating as the proximity sensor, an influence of the reflected light from the display panel of a portable device or the like is present. Thus, the light-receiving surfaces PD02, PD03, PD06, PD07, PD10, PD11, PD14, and PD15 among the light-receiving surfaces PD00 to PD15 resulting from the division into 16 portions are preferably selected as the light-receiving areas (specified areas). Accordingly, the reflected light that is reflected by the fingertip of the user in accordance with the blood flow may stably be obtained.

Sixth Embodiment

A sixth embodiment of the present invention will next be described with reference to FIG. 14. This embodiment is different from the above first to fifth embodiments in a point that the luminance of a backlight that irradiates the display panel such as a liquid crystal panel with light is controlled, for example, based on proximity determination data or illumination data from the proximity illumination sensor that includes the pulse detection function or the proximity sensor that includes the pulse detection function. The descriptions in the first to fifth embodiments apply to the other configurations. For convenience of description, the same reference characters will be given to members that have the same functions as the members illustrated in the drawings associated with the above first to fifth embodiments, and a description thereof will not be made.

Figure 14:
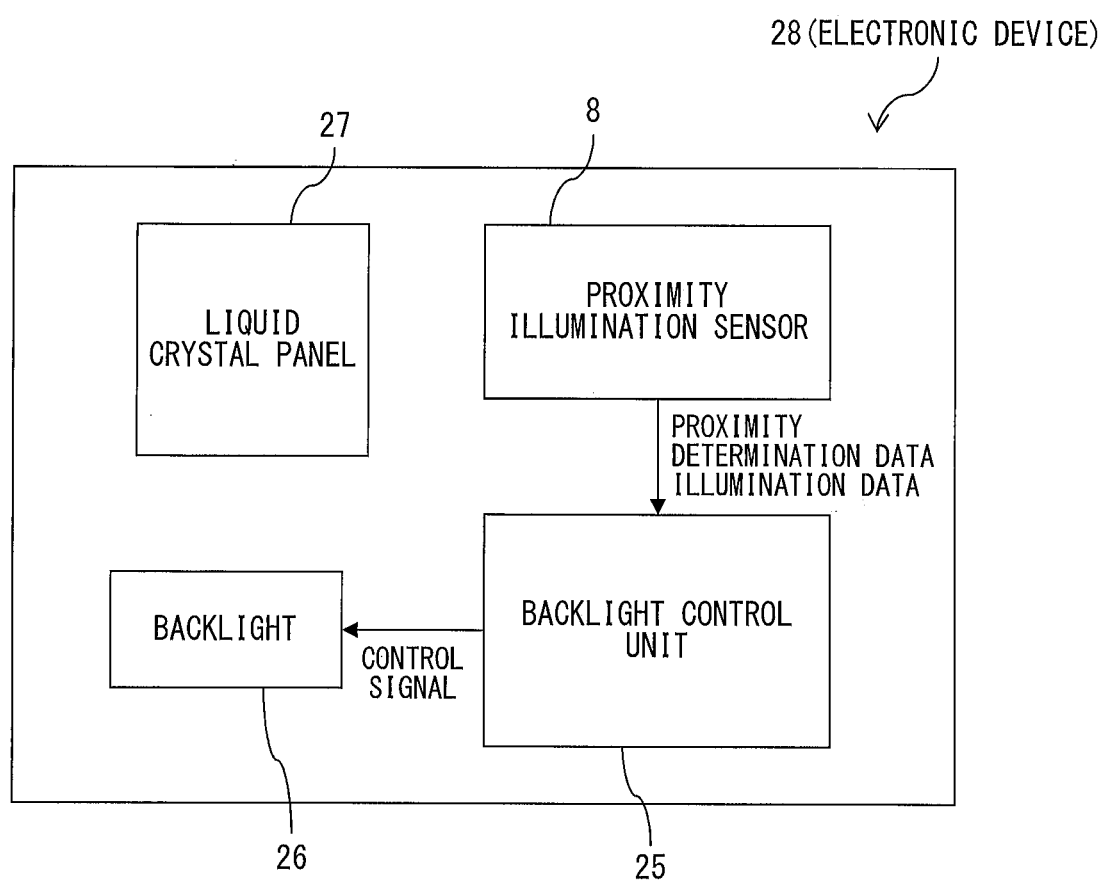
FIG. 14 is a diagram that illustrates a schematic configuration of an electronic device which includes the proximity illumination sensor which includes the pulse detection function, a backlight control unit, a backlight, and a liquid crystal panel.

FIG. 14 is a diagram that illustrates a schematic configuration of an electronic device 28 which includes the proximity illumination sensor 8 which includes the pulse detection function, a backlight control unit 25, a backlight 26, and a liquid crystal panel 27.

As illustrated in the drawing, the luminance of the backlight is controlled via the backlight control unit 25 based on the proximity determination data or the illumination data from the proximity illumination sensor 8 that includes the pulse detection function.

For example, because the illumination data from the proximity illumination sensor 8 that includes the pulse detection function change in accordance with the situation in which the electronic device 28 is placed, the luminance of the backlight is controlled by using the illumination data, and the display quality of the liquid crystal panel 27 may thereby be maintained at a specified level or higher.

Further, in a case where the electronic device 28 is a cellular phone, a smart phone, a digital camera, or the like and where the user moves his/her face or the like to the electronic device 28, the liquid crystal panel 27 may not have to perform display, and control for lowering the luminance of the backlight may thus be performed based on the proximity determination data from the proximity illumination sensor 8 that includes the pulse detection function.

In this embodiment, a description is made about the electronic device as an example. However, in a case of the sensor apparatus, the backlight corresponds to the light-emitting element, and the backlight control unit corresponds to a light-emitting element control unit.

Further, the light-emitting element may be included in the backlight that irradiates the liquid crystal panel or the display panel with light.

In addition, the light-emitting element may be an organic EL light-emitting element.

CONCLUSION

A sensor in a first aspect of the present invention is a sensor that includes a first light-receiving element which receives infrared light and an analog-digital conversion circuit which converts an analog output value of the first light-receiving element to a digital output value, the sensor including an adjustment circuit that performs adjustment such that the digital output value changes in accordance with each value of a distance at least in a prescribed range of the distance between the first light-receiving element and a detected object, and a digital filter that detects a cycle of the digital output value.

The above configuration may realize a sensor that is capable of detecting a pulse of a user by using a proximity illumination sensor or a proximity sensor.

A sensor in a second aspect of the present invention preferably includes a second light-receiving element that receives light in a region of visible light to infrared light.

The above configuration may realize a sensor that is capable of detecting the pulse of the user by using the proximity illumination sensor.

In a sensor in a third aspect of the present invention, it is preferable that the first light-receiving element and the second light-receiving element respectively include a light-receiving element that receives infrared light and a light-receiving element that receives visible light. The first light-receiving element preferably receives light by using the light-receiving element that receives infrared light, and the second light-receiving element preferably receives light by using the light-receiving element that receives infrared light and the light-receiving element that receives visible light.

In the above configuration, the first light-receiving element and the second light-receiving element may be formed with the same structure. Accordingly, the light-receiving elements may more efficiently be formed than forming two light-receiving elements that have different structures.

In a sensor in a fourth aspect of the present invention, the digital filter is preferably configured with a low-pass filter and a high-pass filter.

In the above configuration, an effect of the low-pass filter of smoothing fine noises at high frequencies and an effect of the high-pass filter of removing differences (DC levels) of reflected light amounts due to the users may be obtained. The pulse waveforms resulting from the digital filter process may be obtained as pulse waveforms that have amplitudes with zero being the center, regardless of the users.

In a sensor in a fifth aspect of the present invention, the digital filter preferably has a passband that is the cycle of the pulse.

In a sensor in a sixth aspect of the present invention, the cycle of the digital output value is preferably detected by using a maximum value or a minimum value of the output value from the digital filter.

In a sensor in a seventh aspect of the present invention, the cycle at which the output value from the digital filter becomes zero is preferably set as the cycle of the digital output value.

The above configuration facilitates detection of the cycle of the pulse of the user.

In a sensor in an eighth aspect of the present invention, the first light-receiving element preferably includes plural light-receiving units that are provided by division, and light is preferably received by using the light-receiving units in a prescribed region among the plural light-receiving units.

In the above configuration, a noise light amount due to reflected light from a display panel in a portable device or the like may be reduced.

In a sensor in a ninth aspect of the present invention, the analog-digital conversion circuit is preferably an integrating type analog-digital conversion circuit that performs digital conversion and output of a current amount of an input current from the first light-receiving element in accordance with the light amount of infrared light which is received in a specified time. The integrating type analog-digital conversion circuit preferably includes a charging circuit that has a capacity for storing a charge amount in accordance with the current amount, a discharging circuit that discharges a predetermined charge amount at a time, a comparator circuit that compares an output voltage of the charging circuit with a reference voltage, and a control circuit that outputs a discharge frequency of the discharging circuit based on an output value from the comparator circuit as a digital value.

The above configuration enables analog-digital conversion with a wide dynamic range and high resolution, and enables the fluctuation in the cycle of the pulse to be easily detected.

In a sensor in a tenth aspect of the present invention, the adjustment circuit preferably discharges a predetermined charge amount in a measurement period such that the digital output value changes in accordance with each value of the distance at least in a prescribed range of the distance between the first light-receiving element and the detected object.

The above configuration facilitates a configuration of an offset of the digital output value.

A sensor apparatus in an eleventh aspect of the present invention includes the sensor and a light-emitting element that emits light which includes infrared light.

The above configuration may realize a sensor apparatus that is capable of detecting the pulse of the user by using the proximity illumination sensor or the proximity sensor.

In a sensor apparatus in a twelfth aspect of the present invention, the light-emitting element is preferably controlled based on an output value from the sensor.

The above configuration may realize reduction in power consumption of the sensor apparatus.

In a sensor apparatus in a thirteenth aspect of the present invention, the light-emitting element may be included in a backlight that irradiates a liquid crystal panel with light.

In a sensor apparatus in a fourteenth aspect of the present invention, the light-emitting element may be an organic EL light-emitting element.

An electronic device in a fifteenth aspect of the present invention is an electronic device including a sensor that includes a first light-receiving element which receives infrared light and an analog-digital conversion circuit which converts an analog output value of the first light-receiving element to a digital output value, in which the sensor includes an adjustment circuit that performs adjustment such that the digital output value changes in accordance with each value of a distance at least in a prescribed range of the distance between the first light-receiving element and a detected object, and a digital filter process is performed for the digital output value and a cycle thereof is detected.

The above configuration may realize an electronic device that is capable of detecting the pulse of the user by using the proximity illumination sensor or the proximity sensor.

It should be noted that the present invention is not limited to the above-described embodiments. Various modifications are possible in the scope recited in claims, and embodiments that are obtained by appropriately combining technical means which are disclosed in the different embodiments are included in the technical scope of the present invention.

INDUSTRIAL APPLICABILITY

The present invention may preferably be used for a sensor that includes a proximity sensor, a proximity illumination sensor, or the like, a sensor apparatus that includes the sensor and a light-emitting element which emits light including infrared light, and an electronic device that includes a proximity sensor, a proximity illumination sensor, or the like.

REFERENCE SIGNS LIST 1 infrared light LED (light-emitting element)
2 infrared light targeting photodiode (first light-receiving element)
3 visible light to infrared light targeting photodiode (second light-receiving element)
4 analog-digital conversion circuit
5 count adjustment circuit (adjustment circuit)
6 digital filter
7 analog-digital conversion circuit
8 proximity illumination sensor (sensor)
9 sensor apparatus
10 charging circuit
11 discharging circuit
12 comparator circuit
13 control circuit
14 proximity sensor (sensor)
15 sensor apparatus
16 proximity sensor
17 sensor apparatus
18 electronic device
19 p-substrate to n-well photodiode
20 n-well to p-diffusion photodiode
21 spectral characteristic changeable light-receiving element
22 proximity illumination sensor (sensor)
23 sensor apparatus
24 light-receiving element with a divided light-receiving surface
25 backlight control unit
26 backlight
27 liquid crystal panel (display panel)
28 electronic device

The invention claimed is:

1. A sensor that includes:
a first light-receiving element which receives infrared light; and
an analog-digital conversion circuit which converts an analog output value of the first light-receiving element to a digital output value,
wherein the analog-digital conversion circuit includes
a charging circuit that includes a capacity which stores a charge amount which corresponds to an input current from the first light-receiving element,
a comparator circuit that compares an output voltage of the charging circuit with a reference voltage,
a discharging circuit that discharges a predetermined charge amount at a time from the charge amount of the charging circuit based on an output value from the comparator circuit, and
a counter that outputs a discharge frequency of the discharging circuit as the digital output value, and
the sensor includes:
an adjustment circuit that (i) includes a second discharging circuit that discharges a predetermined charge amount in a measurement period and decides a discharge frequency in accordance with an offset value of the charge amount of the charging circuit and (ii) performs adjustment on the digital output value by offsetting the charge amount of the charging circuit, and
a digital filter that detects a cycle of the digital output value, and
the offset value of the charge amount of the charging circuit is a value that enables an adjustment such that the digital output value is not saturated in a prescribed range of a distance between the first light-receiving element and a detected object.

2. The sensor according to claim 1, wherein the analog-digital conversion circuit includes a control circuit that outputs a control signal which controls discharge of the discharging circuit and includes the counter.

3. The sensor according to claim 1, wherein the digital filter is configured with a low-pass filter and a high-pass filter.

4. The sensor according to claim 1, wherein the cycle of the digital output value is detected by using a maximum value or a minimum value of the output value from the digital filter.

5. A sensor apparatus comprising:
the sensor according to claim 1; and
a light-emitting element that emits light which includes infrared light.

6. The sensor according to claim 1, wherein the counter outputs the discharge frequency of the discharging circuit as the digital output value, the discharge frequency of the discharging circuit being decided in accordance with a charge amount obtained by applying the offset value to the charge amount of the charge circuit.

7. A sensor according to claim 1, wherein the prescribed range is 1 mm to 1.6 mm.

8. An electronic device comprising:
a sensor that includes a first light-receiving element which receives infrared light and an analog-digital conversion circuit which converts an analog output value of the first light-receiving element to a digital output value,
wherein the analog-digital conversion circuit includes
a charging circuit that includes a capacity which stores a charge amount which corresponds to an input current from the first light-receiving element,
a comparator circuit that compares an output voltage of the charging circuit with a reference voltage,
a discharging circuit that discharges a predetermined charge amount at a time from the charge amount of the charging circuit based on an output value from the comparator circuit, and
a counter that outputs a discharge frequency of the discharging circuit as the digital output value,
the sensor includes
an adjustment circuit that (i) includes a second discharging circuit that discharges a predetermined charge amount in a measurement period and decides a discharge frequency in accordance with an offset value of the charge amount of the charging circuit and (ii) performs adjustment on the digital output value by offsetting the charge amount of the charging circuit, the offset value of the charge amount of the charging circuit is a value that enables an adjustment such that the digital output value is not saturated in a prescribed range of a distance between the first light-receiving element and a detected object, and a digital filter process is performed for the digital output value and a cycle thereof is detected.

9. The electronic device according to claim 8, wherein the analog-digital conversion circuit includes a control circuit that outputs a control signal which controls discharge of the discharging circuit and includes the counter.

10. The electronic device according to claim 8, wherein the counter outputs the discharge frequency of the discharging circuit as the digital output value, the discharge frequency of the discharging circuit being decided in accordance with a charge amount obtained by applying the offset value to the charge amount of the charge circuit.

11. An electronic device according to claim 8, wherein the prescribed range is 1 mm to 1.6 mm.

* * * * *